US010420457B2

(12) United States Patent
Chiba

(10) Patent No.: US 10,420,457 B2
(45) Date of Patent: Sep. 24, 2019

(54) ANALYZING APPARATUS

(71) Applicant: HOYA CORPORATION, Tokyo (JP)

(72) Inventor: Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 107 days.

(21) Appl. No.: 15/513,601

(22) PCT Filed: Sep. 16, 2016

(86) PCT No.: PCT/JP2016/077465
§ 371 (c)(1),
(2) Date: Mar. 23, 2017

(87) PCT Pub. No.: WO2017/051779
PCT Pub. Date: Mar. 30, 2017

(65) Prior Publication Data
US 2018/0064320 A1 Mar. 8, 2018

(30) Foreign Application Priority Data
Sep. 24, 2015 (JP) .................. 2015-186553

(51) Int. Cl.
A61B 5/1455 (2006.01)
A61B 1/06 (2006.01)
(Continued)

(52) U.S. Cl.
CPC .......... *A61B 1/0638* (2013.01); *A61B 5/0075* (2013.01); *A61B 5/0084* (2013.01);
(Continued)

(58) Field of Classification Search
CPC ......... G06T 7/0012; G06T 2207/10068; G06T 2207/30024; A61B 5/145; A61B 5/1455;
(Continued)

(56) References Cited

U.S. PATENT DOCUMENTS

2012/0179013 A1 7/2012 Saito
2013/0310688 A1* 11/2013 Rosen ............. A61B 8/08
600/437
(Continued)

FOREIGN PATENT DOCUMENTS

JP 2002-085342 3/2002
JP 5302984 10/2013
(Continued)

OTHER PUBLICATIONS

Mori et al., "Intraoperative Visualization of Cerebral Oxygenation using Hyperspectral Image Data: A Two-Dimensional Mapping Method", Int'l Journal of CARS, vol. 9, Iss. 6, pp. 1059-1072, 2014.*
(Continued)

*Primary Examiner* — Eric F Winakur
*Assistant Examiner* — Darin M Janoschka
(74) *Attorney, Agent, or Firm* — Greenblum & Bernstein, P.L.C.

(57) ABSTRACT

An analyzing apparatus according to an embodiment of the present invention includes: a light source apparatus; an image sensor that generates color image data by capturing an image of biological tissue illuminated by light generated by the light source apparatus; an indicator calculation unit that calculates an indicator X that indicates a feature amount Q of the biological tissue, based on the color image data; and a feature amount acquisition unit that acquires the feature amount Q based on the indicator X. The feature amount acquisition unit includes a contribution calculation unit that calculates a contribution C based on at least two colors of single-color image data included in the color image data, the contribution C of scattering on a spectral characteristic of the biological tissue. Also, the feature amount acquisition unit acquires the feature amount Q based on the indicator X and the contribution C.

16 Claims, 10 Drawing Sheets

(51) Int. Cl.
    *A61B 5/00*   (2006.01)
    *A61B 5/145*  (2006.01)
    *G06T 7/00*   (2017.01)
    *A61B 1/00*   (2006.01)
(52) U.S. Cl.
    CPC ........ *A61B 5/1455* (2013.01); *A61B 5/14546*
            (2013.01); *G06T 7/0012* (2013.01); *A61B
            1/00009* (2013.01); *G06T 2207/10068*
            (2013.01); *G06T 2207/30024* (2013.01)
(58) Field of Classification Search
    CPC . A61B 5/14546; A61B 5/0075; A61B 5/0084;
                    A61B 1/0009; A61B 1/0638
    See application file for complete search history.

(56) References Cited

U.S. PATENT DOCUMENTS

| | | | |
|---|---|---|---|
| 2015/0145978 A1 | 5/2015 | Chiba | |
| 2015/0238126 A1* | 8/2015 | Saito | A61B 5/742 |
| | | | 600/339 |
| 2016/0120449 A1 | 5/2016 | Chiba | |
| 2016/0146723 A1 | 5/2016 | Chiba | |
| 2016/0287063 A1* | 10/2016 | Ramanujam | A61B 1/00082 |

FOREIGN PATENT DOCUMENTS

| | | |
|---|---|---|
| JP | 2016-97067 | 5/2016 |
| WO | 2013/172156 | 11/2013 |
| WO | 2014/192781 | 12/2014 |

OTHER PUBLICATIONS

Acharya et al., "Computational Foundations of Image Interpolation Algorithms", ACM Ubiquity, vol. 8, Article 4, 17 pgs., 2007.*
Zonios et al., "Light Scattering Spectroscopy of Human Skin in Vivo", Optics Express, vol. 17, No. 3, pp. 1256-1267, 2009.*
Bilinear Interpolation (Jul. 16, 2018) in Wikipedia, retrieved Aug. 2, 2018.*
International Search Report issued in International Patent Application No. PCT/JP2016/077465, dated Nov. 1, 2016.

* cited by examiner (a)

(b)

ANALYZING APPARATUS

TECHNICAL FIELD

The present invention relates to an analyzing apparatus that acquires an indicator that indicates the concentration of a biological substance in biological tissue based on a captured image of the biological tissue.

BACKGROUND ART

An endoscope apparatus is known that includes a function for determining the concentration of a biological substance (e.g., hemoglobin) in biological tissue that is the imaging subject, based on color information in an endoscopic image. An example of this type of endoscope apparatus is disclosed in WO 2014/192781 (called "Patent Document 1" hereinafter).

The endoscope apparatus disclosed in Patent Document 1 is an endoscope apparatus that, based on color information in two endoscopic images captured using illumination light in two types of wavelength regions in hemoglobin's absorption band at roughly 550 nm, calculates an indicator that indicates the total hemoglobin amount and an indicator that indicates the degree of oxygen saturation $SatO_2$.

SUMMARY OF INVENTION

Colors in an image of biological tissue are influenced by the scattering of illumination light by the biological tissue. However, in the endoscope apparatus disclosed in Patent Document 1, the calculation of the indicators does not give consideration to change in spectral characteristics arising from scattering. For this reason, there has been a problem that the indicator calculation results vary depending on the amount of scattering (i.e., the calculated indicator values include error arising from scattering).

The present invention was achieved in light of the above-described circumstances, and an object of the present invention is to provide an analyzing apparatus that can compensate for error in an indicator value arising from scattering, and acquire a more precise indicator value.

An analyzing apparatus according to one embodiment of the present invention includes: a light source apparatus; an image sensor that generates color image data by capturing an image of biological tissue illuminated by light generated by the light source apparatus; an indicator calculation unit that calculates an indicator X that indicates a feature amount Q of the biological tissue, based on the color image data; and a feature amount acquisition unit that acquires the feature amount Q based on the indicator X, wherein the feature amount acquisition unit includes a contribution calculation unit that calculates a contribution C based on at least two colors of single-color image data included in the color image data, the contribution C quantifying a degree of contribution of scattering on a spectral characteristic of the biological tissue, and the feature amount acquisition unit acquires the feature amount Q based on the indicator X and the contribution C.

According to this configuration, error arising from scattering is reduced, and it is possible to acquire a more precise indicator value.

The analyzing apparatus described above may have a configuration in which the color image data is RGB color image data, and the contribution calculation unit calculates the contribution C as a ratio of R single-color image data to G or B single-color image data in the color image data.

Also, the analyzing apparatus described above may have a configuration in which the contribution calculation unit includes a storing means for holding information indicating a relationship between the feature amount Q, the indicator X, and the contribution C, and the feature amount acquisition unit acquires the feature amount Q based on the information, the indicator X, and the contribution C.

Also, the analyzing apparatus described above may have a configuration in which the information is a numerical value table or a function that expresses the relationship between the feature amount Q, the indicator X, and the contribution C.

Also, the analyzing apparatus described above may have a configuration in which the information expresses a plurality of sets of the indicator X, the contribution C, and the feature amount Q, and the feature amount acquisition unit selects, from among the plurality of sets, a set that is closest to the indicator X and the contribution C that were calculated based on the color image data, and acquires the feature amount Q of the selected set.

Also, the analyzing apparatus described above may have a configuration in which the information expresses a plurality of sets of the indicator X, the contribution C, and the feature amount Q, the feature amount acquisition unit selects, from among the plurality of sets, two sets that are adjacent to the indicator X and the contribution C that were obtained based on the color image data, and the feature amount acquisition unit calculates the feature amount Q using Expression 1 below $$Q = \frac{X - Xb}{Xa - Xb} \cdot Qa + \frac{Xa - X}{Xa - Xb} \cdot Qb \qquad \text{Expression 1}$$

where
X is an indicator calculated based on the color image data,
Qa is the feature amount of one of the two selected sets,
Xa is the indicator of one of the two selected sets.
Qb is the feature amount of another one of the two selected sets, and
Xb is the indicator of another one of the two selected sets.

Also, the analyzing apparatus described above may have a configuration in which the light source apparatus switches between generating special light for calculating the indicator X and approximately white normal light, and the contribution calculation unit calculates the contribution C based on color image data obtained by capturing an image of the biological tissue illuminated by the normal light.

Also, the analyzing apparatus described above may have a configuration in which the special light includes first special light that has a continuous spectrum distributed in a first wavelength region in which light is absorbed by first and second biological substances included in the biological tissue, and second special light that has a continuous spectrum distributed in a second wavelength region in the first wavelength region, the light source apparatus switches between generating the first special light, the second special light, and the normal light, and the indicator calculation unit calculates the indicator X based on first special observation image data $G_1$ obtained by capturing an image of the biological tissue illuminated by the first special light and second special observation image data $G_2$ obtained by capturing an image of the biological tissue illuminated by the second special light.

Also, the analyzing apparatus described above may have a configuration in which the color image data is RGB color image data, and the first special observation image data $G_1$ and the second special observation image data $G_2$ are each G single-color image data.

Also, the analyzing apparatus described above may have a configuration in which the feature amount Q is a molar concentration ratio of the first and second biological substances included in the biological tissue.

Also, the analyzing apparatus described above may have a configuration in which the first biological substance is oxygenated hemoglobin, the second biological substance is reduced hemoglobin, and the molar concentration ratio is a degree of oxygen saturation.

Also, the analyzing apparatus described above may be configured to include a concentration ratio distribution image generation unit that, based on the feature amount Q, generates a concentration ratio distribution image that shows a distribution of the molar concentration ratio of the first and second biological substances in the biological tissue.

Also, the analyzing apparatus described above may have a configuration in which the feature amount Q is a concentration of a biological substance included in the biological tissue.

Also, the analyzing apparatus described above may be configured to include a concentration distribution image generation unit that, based on the feature amount Q, generates a concentration distribution image that shows a distribution of the concentration of the biological substance included in the biological tissue.

Also, the analyzing apparatus described above may have a configuration in which the feature amount Q is a total hemoglobin amount of the biological tissue.

Also, the analyzing apparatus described above may be configured to include an endoscope in which the image sensor is provided in a distal end portion.

DESCRIPTION OF EMBODIMENTS

Hereinafter, an embodiment of the present invention will be described with reference to the drawings.

An endoscope apparatus according to this embodiment of the present invention described below is an apparatus for quantitatively analyzing biological information (e.g., a degree of oxygen saturation $SatO_2$) of a subject based on multiple images captured under illumination with light of different wavelength regions, and for converting the analysis results into an image and displaying the image. The spectral characteristics of blood (i.e., the spectral characteristics of hemoglobin) have a property of continuously varying according to the degree of oxygen saturation $SatO_2$, and this property is used in the quantitative analysis of the degree of oxygen saturation $SatO_2$ described below.

Spectral characteristics of hemoglobin and principle of calculation of degree of oxygen saturation Before giving a description of the detailed configuration of the endoscope apparatus according to this embodiment of the present invention, the following describes the spectral characteristics of hemoglobin and the principle of the calculation of the degree of oxygen saturation $SatO_2$ in the present embodiment.

Figure 1:
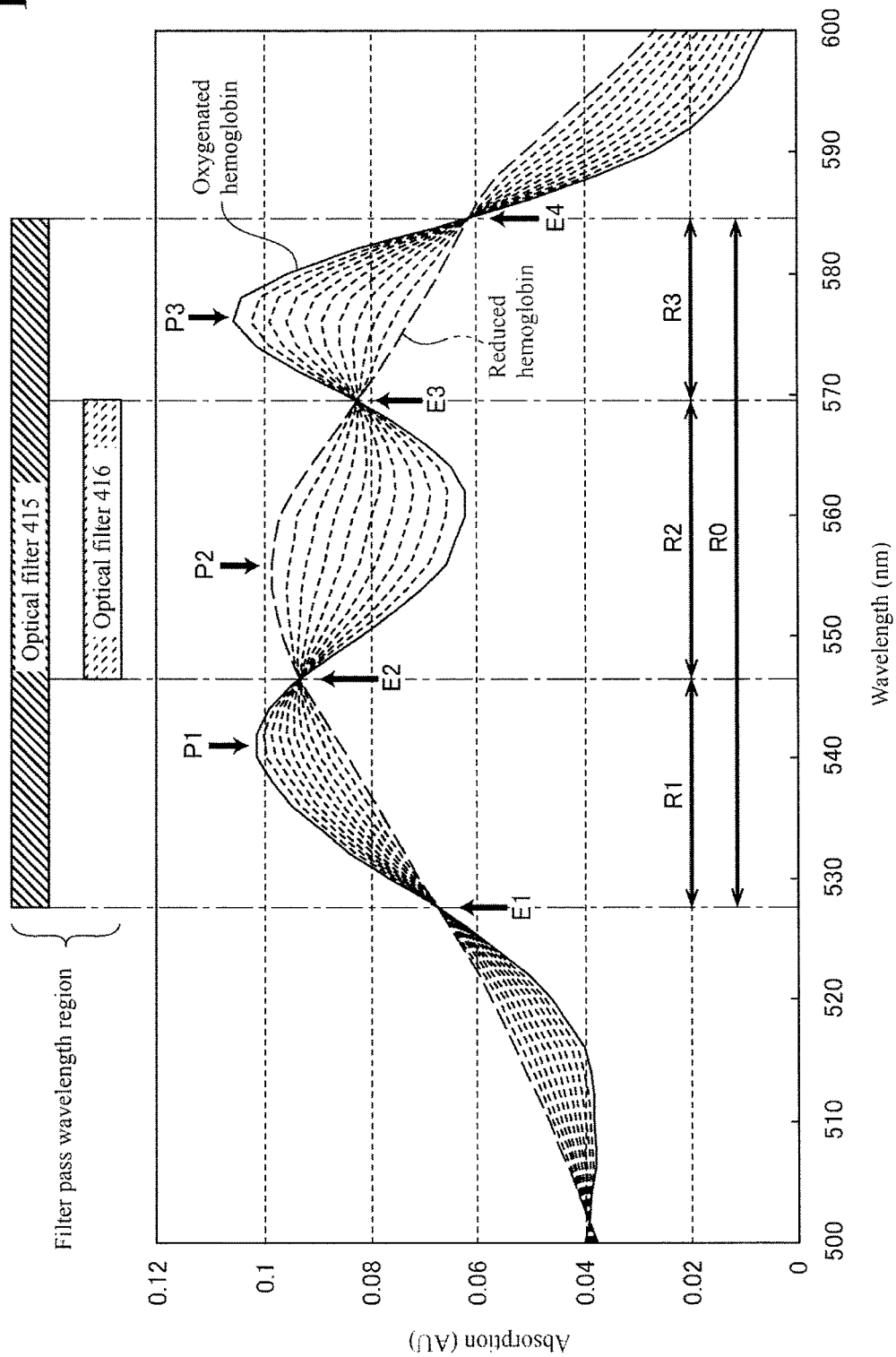
FIG. 1 shows hemoglobin's absorption spectrum at roughly 550 nm.

FIG. 1 shows the absorption spectrum of hemoglobin at roughly 550 nm. Hemoglobin has a strong absorption band at roughly 550 nm deriving from porphyrin. The absorption spectrum of hemoglobin varies according to the degree of oxygen saturation $SatO_2$ (percentage of oxygenated hemoglobin $HbO_2$ in total amount of hemoglobin). The solid line waveform in FIG. 1 is the absorption spectrum in the case where the degree of oxygen saturation $SatO_2$ is 100% (i.e., the absorption spectrum of oxygenated hemoglobin $HbO_2$), and the long dashed line waveform is the absorption spectrum in the case where the degree of oxygen saturation $SatO_2$ is 0% (i.e., the absorption spectrum of reduced hemoglobin Hb). Also, the short dashed lines are the absorption spectrums of hemoglobin (mixture of oxygenated hemoglobin $HbO_2$ and reduced hemoglobin Hb) at intermediate degrees of oxygen saturation $SatO_2$ (10, 20, 30, . . . 90%).

As shown in FIG. 1, in the absorption band at roughly 550 nm, oxygenated hemoglobin $HbO_2$ and reduced hemoglobin Hb (also called deoxygenated hemoglobin) have mutually different peak wavelengths. Specifically, oxygenated hemoglobin $HbO_2$ has an absorption peak P1 at a wavelength of roughly 542 nm and an absorption peak P3 at a wavelength of roughly 576 nm. On the other hand, reduced hemoglobin Hb has an absorption peak P2 at roughly 556 nm. FIG. 1 shows a two-component absorption spectrum in which the sum of the concentrations of the respective components (oxygenated hemoglobin $HbO_2$ and reduced hemoglobin Hb) is constant, and therefore isosbestic points E1, E2, E3, and E4, at which the absorption is constant regardless of the concentrations of the respective components (i.e., the degree of oxygen saturation $SatO_2$), appear in the spectrum. In the following description, the wavelength region sandwiched between the isosbestic points E1 and E2 will be called a wavelength region R1, the wavelength region sandwiched between the isosbestic points E2 and E3 will be called a wavelength region R2, and the wavelength region sandwiched between the isosbestic points E3 and E4 will be called a wavelength region R3. Also, the wavelength region sandwiched between the isosbestic points E1 and E4 (i.e., the combination of the wavelength regions R1, R2, and R3) will be called a wavelength region R0.

As shown in FIG. 1, in the regions between adjacent isosbestic points, absorption monotonically increases or decreases relative to the degree of oxygen saturation $SatO_2$. Also, in the regions between adjacent isosbestic points, the absorption of hemoglobin changes roughly linearly relative to the degree of oxygen saturation $SatO_2$.

Specifically, hemoglobin absorptions $A_{R1}$ and $A_{R3}$ in the wavelength regions R1 and R3 linearly increase monotonically relative to the concentration of oxygenated hemoglobin $HbO_2$ (or the degree of oxygen saturation $SatO_2$), and a hemoglobin absorption $A_{R2}$ in the wavelength region R2 linearly increases monotonically relative to the concentration of reduced hemoglobin Hb (1-degree of oxygen saturation $SatO_2$). Accordingly, an indicator X defined by Expression 2 below linearly increases monotonically relative to the concentration of oxygenated hemoglobin $HbO_2$ (or the degree of oxygen saturation $SatO_2$).

$$X=(A_{R1}+A_{R3})-A_{R2} \quad \text{Expression 2}$$

Expression 2 above defines the indicator X by the difference in absorption between bands in which the increase/decrease behavior relative to the degree of oxygen saturation $SatO_2$ is different, but the indicator X can be defined by a different expression as long as there is a monotone (more preferably, a linear) quantitative relationship with the degree of oxygen saturation $SatO_2$. For example, as shown in Expression 3 below, the ratio of the sum of the absorptions $A_{R1}$ and $A_{R3}$, which monotonically increase relative to the degree of oxygen saturation $SatO_2$, and the absorption $A_{R2}$, which monotonically decreases relative to the degree of oxygen saturation $SatO_2$, linearly increases monotonically relative to the degree of oxygen saturation $SatO_2$, and therefore this ratio is a good indicator of degree of oxygen saturation $SatO_2$.

$$X=(A_{R1}+A_{R3})/A_{R2} \quad \text{Expression 3}$$

Accordingly, as long as a quantitative relationship between the degree of oxygen saturation $SatO_2$ and the indicator X is acquired empirically in advance, the degree of oxygen saturation $SatO_2$ can be calculated from the value of the indicator X.

Configuration of Endoscope Apparatus

Figure 2:
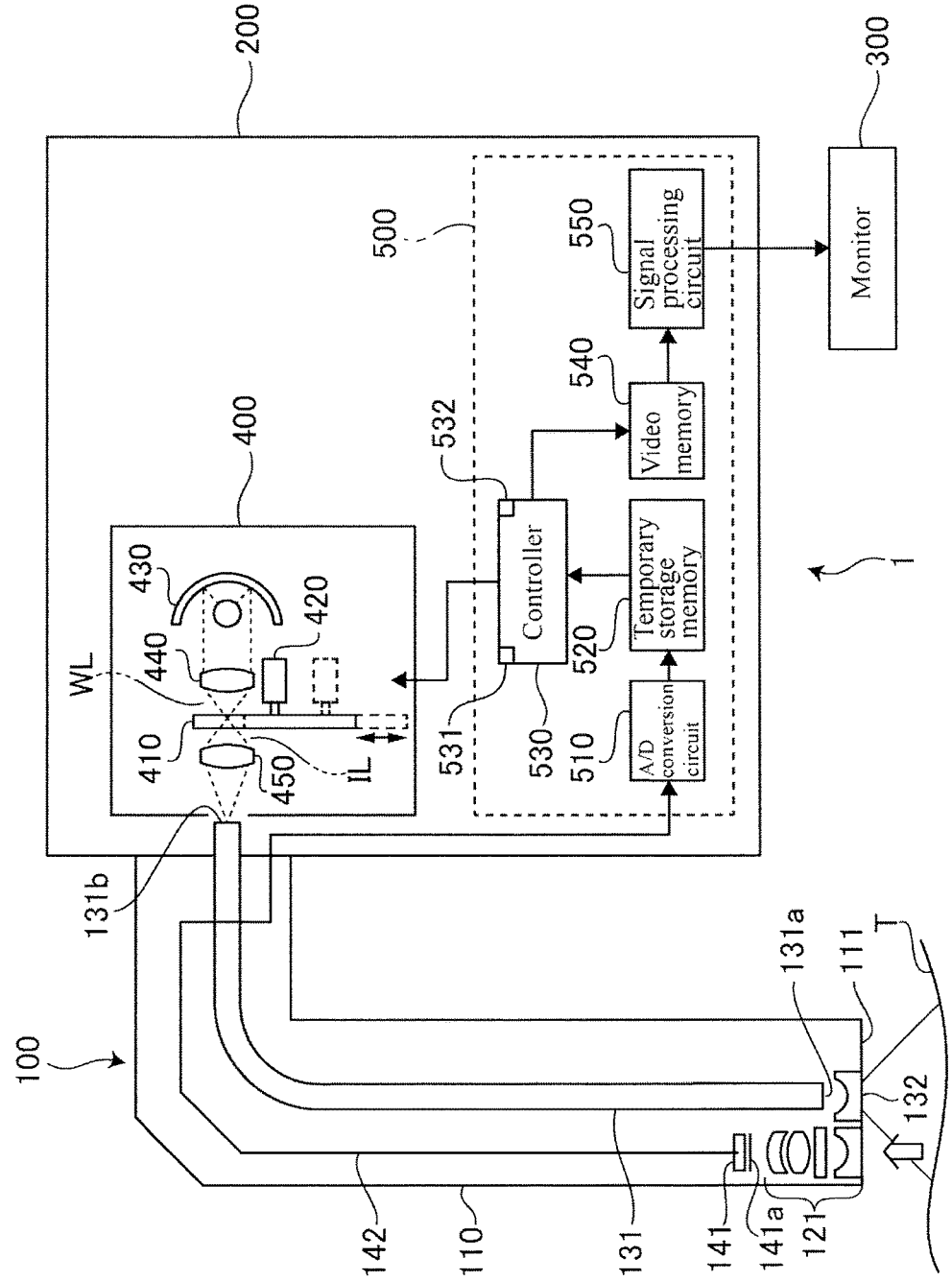
FIG. 2 is a block diagram of an endoscope apparatus according to an embodiment of the present invention.

FIG. 2 is a block diagram of an endoscope apparatus 1 according to this embodiment of the present invention. The endoscope apparatus 1 of the present embodiment includes an electronic endoscope 100, a processor 200, and a monitor 300. The electronic endoscope 100 and the monitor 300 are detachably connected to the processor 200. Also, a light source unit 400 and an image processing unit 500 are built into the processor 200.

The electronic endoscope 100 has an insertion portion 110 for insertion into a body cavity. The electronic endoscope 100 is internally provided with a light guide 131 that extends over approximately the entire length thereof. One end portion (distal end portion 131a) of the light guide 131 is arranged in the vicinity of the distal end portion of the insertion portion 110 (insertion distal end portion 111), and the other end portion (base end portion 131b) of the light guide 131 is connected to the processor 200. The light source unit 400 built into the processor 200 includes a light source lamp 430 that generates high-intensity white light WL. A xenon lamp, a metal halide lamp, an LED lamp, a halogen lamp, or the like is used as the light source lamp 430. The illumination light IL generated by the light source unit 400 enters the base end portion 131b of the light guide 131, passes through the light guide 131 and is guided to the distal end portion 131a, and then exits from the distal end portion 131a. A light distribution lens 132 arranged opposing the distal end portion 131a of the light guide 131 is provided at the insertion distal end portion 111 of the electronic endoscope 100, and illumination light IL that exits the distal end portion 131a of the light guide 131 passes through the light distribution lens 132 and illuminates biological tissue T in the vicinity of the insertion distal end portion 111.

Also, the insertion distal end portion 111 is provided with an objective optical system 121 and an image sensor 141. Part of the light reflected and scattered by the surface of the biological tissue T (returning light) enters the objective optical system 121, is condensed, and forms an image on the light receiving surface of the image sensor 141. The image sensor 141 of the present embodiment is a CCD (Charge Coupled Device) image sensor for color image capturing, and includes a color filter 141a on its light receiving surface, but another type of image sensor such as a CMOS (Complementary Metal Oxide Semiconductor) image sensor may be used. The color filter 141a includes an array of R filters that allow red light to pass (penetrate), G filters that allow green light to pass, and B filters that allow blue light to pass, and is a so-called on-chip filter that is formed directly on the light receiving element of the image sensor 141. The R, G, and B filters of the color filter 141a have the spectral characteristics shown in FIG. 3. Specifically, the R filters of the present embodiment are filters that allow light with a wavelength longer than approximately 570 nm to pass, the G filters are filters that allow light with a wavelength of approximately 470 nm to 620 nm to pass, and the B filters are filters that allow light with a wavelength shorter than approximately 530 nm to pass.

The image sensor 141 is controlled to operate in synchronization with a signal processing circuit 550 that will be described later, and periodically (e.g., at intervals of 1/30 second) outputs an imaging signal that corresponds to the image formed on the light receiving surface. The imaging signal output from the image sensor 141 is sent to the image processing unit 500 of the processor 200 via a cable 142.

The image processing unit 500 includes an A/D conversion circuit 510, a temporary storage memory 520, a controller 530, a video memory 540, and a signal processing circuit 550. The A/D conversion circuit 510 performs A/D conversion on an imaging signal received from the image sensor 141 of the electronic endoscope 100, and outputs the obtained digital image data. The digital image data output from the A/D conversion circuit 510 is sent to and stored in the temporary storage memory 520.

This digital image data includes R digital image data obtained by the light receiving elements on which the R filters are mounted, G digital image data obtained by the light receiving elements on which the G filters are mounted, and B digital image data obtained by the light receiving elements on which the B filters are mounted. In the present specification, the R digital image data, the G digital image data, and the B digital image data will also be called single-color image data (R single-color image data. G single-color image data, and B single-color image data).

The controller 530 processes one or more pieces of digital image data stored in the temporary storage memory 520 to generate one piece of display image data, and sends the display image data to the video memory 540. For example, the controller 530 generates a reflection spectrum for the biological tissue T for each pixel (x,y) based on display image data generated from one piece of digital image data, based on display image data in which multiple pieces of digital image data are arranged side-by-side, or based on multiple pieces of digital image data, then uses the reflection spectrum to generate display image data that identifies and displays healthy sites and lesion sites or generate display image data that displays a graph of the reflection spectrum of the biological tissue T that corresponds to a certain pixel (x,y), and then stores the display image data in the video memory 540. The signal processing circuit 550 generates a video signal in a predetermined format (e.g., a format compliant with NTSC standards or DVI standards) based on the display image data stored in the video memory 540, and outputs the video signal. The video signal output from the signal processing circuit 550 is received by the monitor 300. An endoscopic image or the like captured by the electronic endoscope 100 is then displayed on the monitor 300.

In this way, the processor 200 includes both functionality as a video processor that processes imaging signals output from the image sensor 141 of the electronic endoscope 100, and functionality as a light source apparatus that supplies illumination light IL, which is for illuminating biological tissue T that is the imaging subject, to the light guide 131 of the electronic endoscope 100.

Besides the above-described light source 430, the light source unit 400 also includes a condensing lens 440, a rotating filter 410, a filter control unit 420, and a condensing lens 450. Approximately parallel white light WL that exits the light source 430 is condensed by the condensing lens 440, passes through the rotating filter 410, is then again condensed by the condensing lens 450, and then enters the base end portion 131b of the light guide 131. The rotating filter 410 can be moved between an application position (solid lines) on the optical path of the white light WL and a retracted position (dashed lines) off the optical path by a moving means (not shown) such as a linear guideway.

Note that the configuration of the light source unit 400 is not limited to the configuration shown in FIG. 2. For example, a lamp that generates convergent light may be employed as the light source 430. In this case, a configuration may be employed in which, for example, white light WL is condensed before reaching the condensing lens 440, and then caused to enter the condensing lens 440 as diffused light. Also, a configuration may be employed in which the condensing lens 440 is not used, and convergent light from the light source 430 is condensed in the vicinity of the rotating filter 410.

Also, a configuration may be employed in which the condensing lens 440 is not used, and approximately parallel light generated by the light source 430 is caused to directly enter the rotating filter 410.

Also, in the case of using a lamp that generates convergent light, a configuration may be employed in which a collimator lens is used instead of the condensing lens 440 in order to cause white light WL that is in an approximately parallel state to enter the rotating filter 410. For example, in the case of using an interference type of optical filter such as a dielectric multilayer filter as the rotating filter 410, by causing approximately parallel white light WL to enter the rotating filter 110, the angle of incidence of the white light WL on the optical filter can be made uniform, thus making it possible to obtain more favorable filter characteristics.

Also, a lamp that generates diverging light may be applied as the light source 430. In this case as well, a configuration can be employed in which a collimator lens is used instead of the condensing lens 440 in order to cause approximately parallel white light WL to enter the rotating filter 410.

The rotating filter 410 is a disc-type optical unit that includes multiple optical filters, and is configured such that the pass wavelength region is switched according to the rotation angle (or phase). The rotation angle of the rotating filter 110 is controlled by the filter control unit 420, which is connected to the controller 530. The controller 530 controls the rotation angle of the rotating filter 410 via the filter control unit 420, thus switching the spectrum of illumination light that passes through the rotating filter 410 and is supplied to the light guide 131.

Figure 4:
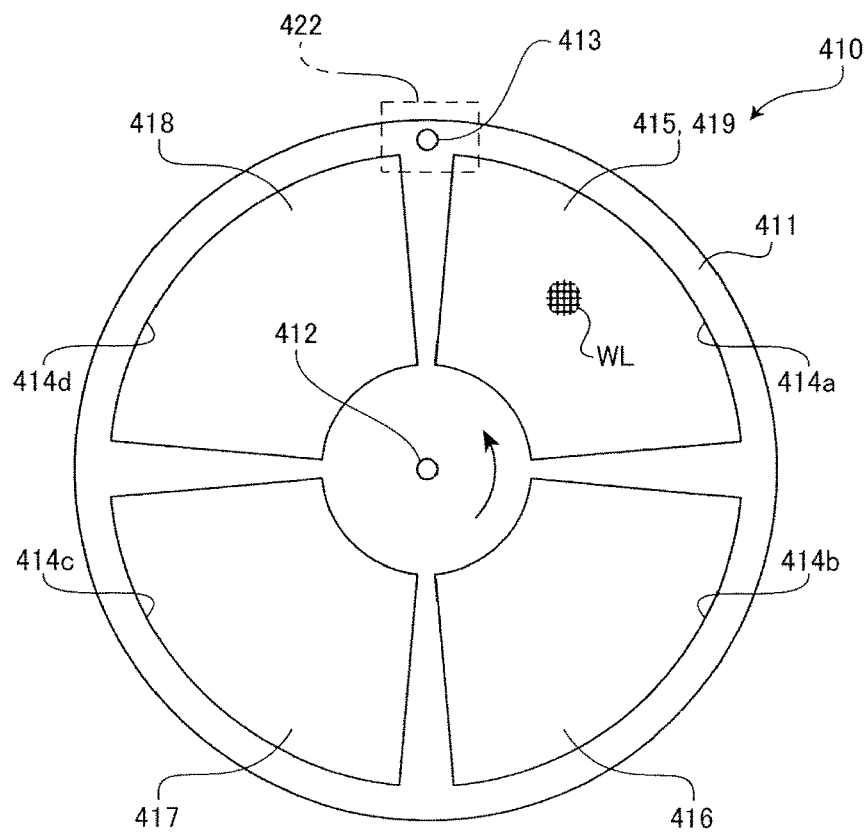
FIG. 4 is an external view of a rotating filter.

FIG. 4 is an external view (front view) of the rotating filter 410. The rotating filter 410 includes an approximately disc-shaped frame 411 and four optical filters 415, 416, 417, and 418 that are shaped as circular fans. Four windows 414a, 414b, 414c, and 414d that are shaped as circular fans are formed with equal gaps therebetween around the central axis of the frame 411, and the optical filters 415, 416, 417, and 418 are respectively fitted into the windows 414a, 414b, 414c, and 414d. Note that the optical filters of the present embodiment are all dielectric multilayer filters, but another type of optical filter (e.g., an absorption optical filter or an etalon filter that uses a dielectric multilayer film as a reflection film) may be used.

Also, a boss hole 412 is formed on the central axis of the frame 411. An output shaft of the filter control unit 420 is inserted in and fixed to the boss hole 412, and the rotating filter 410 rotates along with the output shaft of the filter control unit 420.

Although the state where white light WL enters the optical filter 415 is shown in FIG. 4, when the rotating filter 410 rotates in the direction indicated by the arrow, the optical filter that the white light WL enters successively switches between the optical filters 415, 416, 417, and 418 in this order, and thus the spectrum of illumination light IL that passes through the rotating filter 410 switches.

The optical filters 415 and 416 are optical bandpass filters that selectively allow light in the 550 nm band to pass. As shown in FIG. 1, the optical filter 415 is configured to allow light in the wavelength region from the isosbestic points E1 to E4 (i.e., the wavelength region R0 (also called the "first illumination wavelength region")) to pass with low loss, and block light in other wavelength regions. Also, the optical filter 416 is configured to allow light in the wavelength region from the isosbestic points E2 to E3 (i.e., the wavelength region R2 (also called the "second illumination wavelength region")) to pass with low loss, and block light in other wavelength regions.

As shown in FIG. 1, the wavelength region R1 includes the peak wavelength of the absorption peak P1 derived from oxygenated hemoglobin $HbO_2$, the wavelength region R2 includes the peak wavelength of the absorption peak P2 derived from reduced hemoglobin Hb, and the wavelength region R3 includes the peak wavelength of the absorption peak P3 derived from oxygenated hemoglobin $HbO_2$. Also, the wavelength region R0 includes the peak wavelengths of the absorption peaks P1, P2, and P3.

Figure 3:
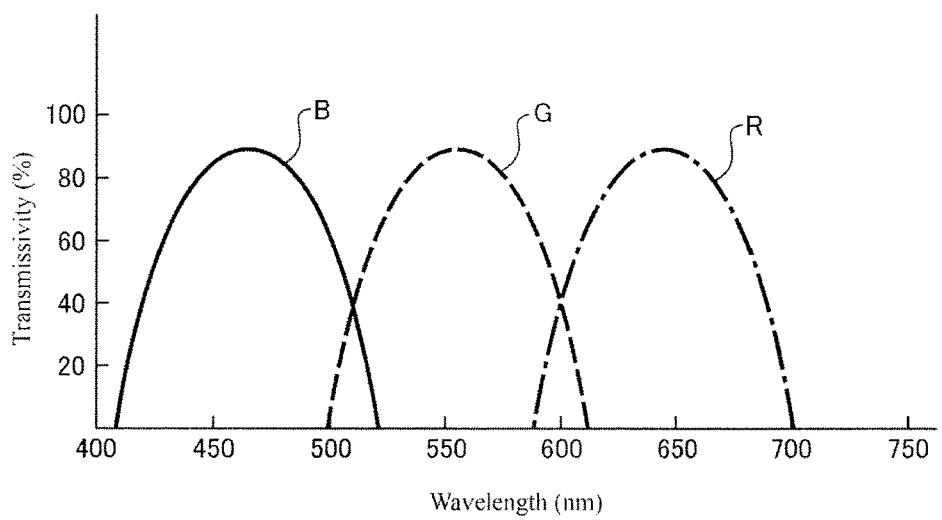
FIG. 3 shows the transmission spectrum of color filters included in an image sensor.

The pass wavelength regions of the optical filters 415 and 416 (FIG. 1) are included in the pass wavelength region of the G filters of the color filter 141a (FIG. 3). Accordingly, an image formed on the light receiving surface of the image sensor 141 by light that passes through the optical filters 415 and 416 is received by the light receiving elements on which the G filters are mounted, and is obtained as G digital image data.

The optical filter 417 is designed to selectively allow the passage of only light in the 650 nm band (630 to 650 nm), which is a wavelength region with low absorption by hemoglobin. The pass wavelength region of the optical filter 417 is included in the pass wavelength region of the R filters of the color filter 141a (FIG. 3). Accordingly, an image formed by light that. passes through the optical filters 417 is received by the light receiving elements on which the R filters are mounted, and is obtained as R digital image data. Image data acquired using illumination light in the 650 nm band is used in later-described standardization processing.

Also, the optical filter 418 is an ultraviolet cut filter, and illumination light IL that passes through the optical filter 418 (i.e., white light) is used in the capture of a normal observation image. Note that a configuration is possible in which the optical filter 418 is not used, and the windows 414d of the frame 411 is open. Also, in the present specification, illumination light that passes through the optical filter 415, 416, or 417 is also called special light (or special observation light), and white light (or wide band light) that passes through the optical filter 418 is also called normal light (or normal observation light).

A light attenuation filter (ND filter) 419 is attached over the optical filter 415 in the window 414a. The light attenuation filter 419 has almost no wavelength dependency over the entire visible light range, and merely reduces the quantity of light with almost no change in the spectrum of illumination light IL. By using the light attenuation filter 419, the quantity of illumination light IL that passes through the optical filter 415 and the light attenuation filter 419 is adjusted to approximately the same as the quantity of illumination light IL that passes through the optical filter 416. Accordingly, regardless of whether illumination light IL that passed through the optical filter 415 or the optical filter 416 is used, it is possible to capture an image with the same exposure time and appropriate exposure.

In the present embodiment, a fine metal mesh is used as the light attenuation filter 419. Besides a metal mesh, another type of light attenuation filter such as a reflection or absorption type may be used. Also, a configuration is possible in which a light attenuation filter is not used, and the passage rates of the optical filters 415 and 416 themselves are adjusted. Also, a light attenuation filter may be attached to the windows 414c and 414d as well. Moreover, the passing light quantity may be adjusted by changing the central angles (i.e., opening areas) of the windows 414a to 414d. Furthermore, a configuration is possible in which a light attenuation filter is not used, and the exposure time is adjusted for each optical filter that is used.

A through-hole 413 is formed in the peripheral edge portion of the frame 411. The through-hole 413 is formed at the same rotation position as the boundary portion between the window 414a and the window 414d. A photo interrupter 422 for detecting the through-hole 413 is arranged in the periphery of the frame 411 so as to surround a portion of the peripheral edge portion of the frame 411. The photo interrupter 422 is connected to the filter control unit 420.

The endoscope apparatus 1 of the present embodiment has four operating modes, namely a normal observation mode, a spectral analysis (degree of oxygen saturation distribution image display) mode, a baseline measurement mode, and a calibration mode. These operating modes are switched by a user operation. The normal observation mode is an operating mode for capturing color images using white light that passes through the optical filter 418. The spectral analysis mode is a mode for performing spectral analysis based on digital image data obtained using illumination light that passes through the optical filters 415, 416, and 417, and displaying a biomolecule distribution image of biological tissue (e.g., a degree of oxygen saturation distribution image). The baseline measurement mode is a mode for, before (or after) performing actual endoscopic observation, using a color reference board such as an achromatic diffuser (e.g., frosted glass) or a standard reflector as the imaging subject, performing imaging using illumination light that passes through the optical filters 415, 416, and 417, and acquiring data for use in later-described standardization processing. The calibration mode is processing for performing spectral analysis on a standard sample whose characteristic such as the degree of oxygen saturation $SatO_2$ is already known, and adjusting a parameter (later-described correction coefficient k) so as to cancel out the difference between an analysis result and the reference quantity (or theoretical value) of the characteristic of the standard sample.

In the normal observation mode, the controller 530 controls the moving means to move the rotating filter 410 from the application position to the retracted position. Note that in the operating modes other than the normal observation mode, the rotating filter 410 is arranged at the application position. Also, in the case where the rotating filter 410 does not have a moving means, the controller 530 controls the filter control unit 420 to stop the rotating filter 410 at a position at which white light WL enters the optical filter 418. Then, digital image data obtained by the image sensor 141 is subjected to image processing as necessary, and then converted into a video signal and displayed on the monitor 300.

In the spectral analysis mode, the controller 530 controls the filter control unit 420 to drive the rotating filter 410 to rotate at a constant rotational frequency and successively capture images of the biological tissue T using illumination light that passes through the optical filters 415, 416, 417, and 418. An image that shows the distribution of biomolecules in the biological tissue is then generated based on digital image data obtained using the optical filters 415, 416, and 417, and then a display screen that arranges the generated image and the normal observation image obtained using the optical filter 418 side-by-side is generated, converted into a video signal, and displayed on the monitor 300.

In the spectral analysis mode, the filter control unit 420 detects the phase of rotation of the rotating filter 410 based on the timing of detection of the through-hole 413 by the photo interrupter 422, compares the detected phase with the phase of a timing signal supplied by the controller 530, and adjusts the phase of rotation of the rotating filter 410. The timing signal from the controller 530 is synchronized with the drive signal for the image sensor 141. Accordingly, the rotating filter 410 is driven to rotate at a substantially constant rotational frequency in synchronization with the driving of the image sensor 141. Specifically, the rotation of the rotating filter 410 is controlled such that the one of the optical filters 415 to 418 (windows 414a-d) that white light WL enters is switched each time one image (three R, G, and B frames) is captured by the image sensor 141.

In the baseline measurement mode, the controller 530 controls the filter control unit 420 to rotate the rotating filter 410 and successively capture images of a color reference board using illumination light IL that passes through the optical filters 415, 416, and 417. Pieces of G digital image data obtained using illumination light IL that passes through the optical filters 415 and 416 are stored in an internal memory 531 of the controller 530 as baseline image data pieces $BL_{415}(x,y)$ and $BL_{416}(x,y)$. Also, R digital image data obtained using illumination light. IL that passes through the optical filter 417 is stored in the internal memory 531 of the controller 530 as baseline image data $BL_{417}(x,y)$.

Figure 5:
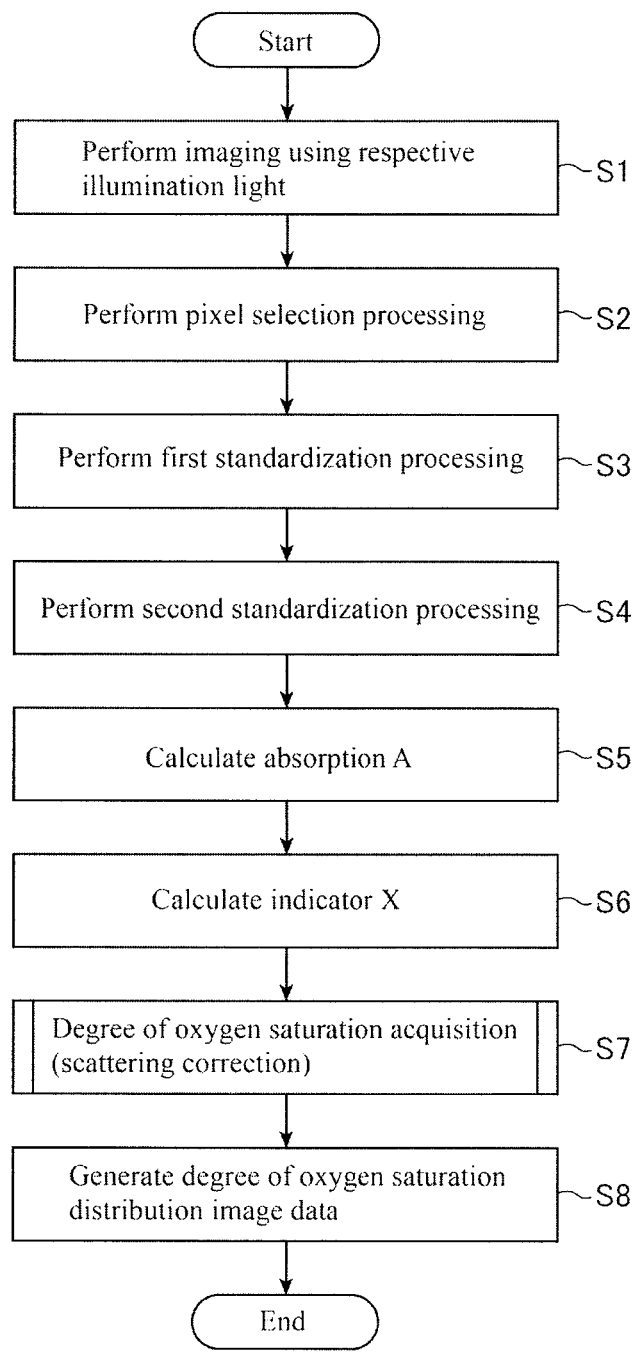
FIG. 5 is a flowchart showing image generation processing according to the embodiment of the present invention.

Next, image generation processing executed by the image processing unit 500 in the spectral analysis mode will be described. Note that the image processing unit 500 calculates the indicator X according to this embodiment of the present invention as will be described later, and therefore will also be called an "indicator calculation unit". Also, the image processing unit 500 acquires a degree of oxygen saturation $SatO_2$ and a total hemoglobin amount, which are feature amounts of biological tissue, based on the indicator X as will be described later, and therefore will also be called a "feature amount acquisition unit". FIG. 5 is a flowchart showing image generation processing (include indicator calculation processing and feature amount acquisition processing).

If the spectral analysis mode has been selected, the filter control unit 420 drives the rotating filter 410 to rotate at a constant rotational frequency as described above. Illumination light IL is successively supplied from the light source unit 400, and then through the optical filters 415, 416, 417, and 418, and images are successively captured using the respective types of illumination light IL (processing S1). Specifically, G digital image data $G_{415}(x,y)$ obtained using illumination light IL that passes through the optical filter 415, G digital image data $G_{416}(x,y)$ obtained using illumination light IL that passes through the optical filter 416, R digital image data $R_{417}(x,y)$ obtained using illumination light IL that passes through the optical filter 417, and R digital image data $R_{418}(x,y)$, G digital image data $G_{418}(x,y)$, and B digital image data $B_{418}(x,y)$ obtained using illumination light IL (white light) that passes through the optical filter (ultraviolet cut filter) 418 are stored in the internal memory 532 of the controller 530.

Next the image processing unit 500 performs pixel selection processing S2 for selecting pixels that are to be subjected to subsequent analysis processing (processing S3-S8), using the R digital image data $R_{418}(x,y)$, the G digital image data $G_{418}(x,y)$, and the B digital image data $B_{418}(x,y)$ acquired in processing S1. At locations where blood is not included, or locations where the tissue color is dominantly influenced by a substance other than hemoglobin, even if the degree of oxygen saturation $SatO_2$ or blood flow is calculated based on color information of the pixel, a meaningful value is not obtained, but rather is simply noise. If such noise is calculated and presented to a physician, it will not only be a hindrance to the physician's diagnosis, but also have the harmful effect of placing an unnecessary burden on the image processing unit 500 and reducing the processing speed. In view of this, the image generation processing of the present embodiment is configured such that pixels suited to analysis processing (i.e., pixels whose color information is suitable to the spectroscopic features of hemoglobin) are selected, and analysis processing is performed on only the selected pixels.

In pixel selection processing S2, only pixels that satisfy all of the conditions of Expressions 4, 5, and 6 below are selected as target pixels for analysis processing.

$$B_{418}(x, y)/G_{418}(x, y) > a_1 \quad \text{Expression 4}$$

$$R_{418}(x, y)/G_{418}(x, y) > a_2 \quad \text{Expression 5}$$

$$R_{418}(x, y)/B_{418}(x, y) > a_3 \quad \text{Expression 6}$$

Here, $a_1$, $a_2$, and $a_3$ are positive constants.

The above three conditional expressions are set based on the magnitude relationship between the color component values in color images of blood (G component<B component<R component). Note that pixel selection processing S2 may be performed using only one or two of the above three conditional expressions (e.g., using only Expressions 5 and 6 when focusing on the color red which is specific to blood).

Next, the image processing unit 500 performs standardization processing. The standardization processing of the present embodiment includes first standardization processing S3 for correcting characteristics of the endoscope apparatus 1 itself (e.g., optical filter transmissivity and image sensor light sensitivity), and a second standardization processing S4 for correcting variation in reflectance caused by the surface state of the biological tissue T that is the imaging subject or differences in the angle of incidence of illumination light IL on the biological tissue T.

In this standardization processing, the image processing unit 500 uses Expression 7 below to calculate a standardization reflectance $SR_{415}(x,y)$ based on the G digital image data $G_{415}(x,y)$ obtained using illumination light IL that passes through the optical filter 415, the R digital image data $R_{417}(x,y)$ obtained using illumination light IL that passes through the optical filter 417, and the baseline image data $BL_{415}(x,y)$ and $BL_{417}(x,y)$. Note that by dividing the pieces of digital image data $G_{415}(x,y)$ and $R_{417}(x,y)$ by the corresponding pieces of baseline image data $BL_{415}(x,y)$ and $BL_{417}(x,y)$, an element dependent on the characteristics of the endoscope apparatus 1 (instrumental function) is removed (first standardization processing S3). Also, dividing the G digital image data $G_{415}(x,y)$ by the R digital image data $R_{417}(x,y)$ corrects variation in reflectance caused by the surface state of the biological tissue T or differences in the angle of incidence of illumination light IL on the biological tissue T (second standardization processing S4).

$$SR_{415}(x, y) = \frac{G_{415}(x, y)/BL_{415}(x, y)}{R_{417}(x, y)/BL_{417}(x, y)} \quad \text{Expression 7}$$

Similarly, a standardization reflectance $SR_{416}(x,y)$ is calculated using Expression 8 below.

$$SR_{416}(x, y) = \frac{G_{416}(x, y)/BL_{416}(x, y)}{R_{417}(x, y)/BL_{417}(x, y)} \quad \text{Expression 8}$$

Expressions 9 and 10 below are used to respectively calculate absorptions $A_{415}(x,y)$ and $A_{416}(x,y)$ of the biological tissue T with respect to illumination light IL that passes through the optical filters 415 and 416 (processing S5).

$$A_{415}(x, y) = -\log[SR_{415}(x, y)] \quad \text{Expression 9}$$

$$A^{416}(x, y) = -\log[SR_{416}(x, y)] \quad \text{Expression 10}$$

Note that the absorptions $A_{415}(x,y)$ and $A_{416}(x,y)$ can also be approximately calculated using Expressions 11 and 12 below.

$$A_{415}(x, y) = -SR_{415}(x, y) \quad \text{Expression 11}$$

$$A_{416}(x, y) = -SR_{416}(x, y) \quad \text{Expression 12}$$

Also, it is possible to omit the above-described standardization processing (processing S3, S4) and perform simple spectral analysis. In this case, the absorptions $A_{415}(x,y)$ and $A_{416}(x,y)$ are calculated using Expressions 13 and 14 below.

$$A_{415}(x, y) = -\log G_{415}(x, y) \quad \text{Expression 13}$$

$$A_{416}(x, y) = -\log G_{416}(x, y) \quad \text{Expression 14}$$

Also, in this case, the absorptions $A_{415}(x,y)$ and $A_{416}(x,y)$ can also be approximately calculated using Expressions 15 and 16 below.

$$A_{415}(x, y) = -G_{415}(x, y) \quad \text{Expression 15}$$

$$A_{416}(x, y) = -G_{416}(x, y) \quad \text{Expression 16}$$

Also, as is clear from the relationship between the hemoglobin absorption wavelength regions R1, R2, and R3 and the pass wavelength regions of the optical filters 415 and 416 shown in 11.G. 1, the relationships shown in Expressions 17 and 18 below exist between the absorptions $A_{R1}(x,y)$, $A_{R2}(x,y)$, and $A_{R3}(x,y)$ of the biological tissue T with respect to the wavelength regions R1, R2, and R3 and the absorptions $A_{415}(x,y)$ and $A_{416}(x,y)$ of the biological tissue T with respect to illumination light IL that passes through the optical filters 415 and 416.

$$A_{R1}(x, y) + A_{R3}(x, y) = A_{415}(x, y) - kA_{416}(x, y) \quad \text{Expression 17}$$

$$A_{R2}(x, y) = kA_{416}(x, y) \quad \text{Expression 18}$$

Accordingly, the indicator X (Expression 2) is expressed by Expression 19 below.

$$X(x, y) = [A_{R1}(x, y) + A_{R3}(x, y)] - A_{R2}(x, y) \quad \text{Expression 19}$$
$$= [A_{415}(x, y) - kA_{416}(x, y)] - kA_{416}(x, y)$$
$$= A_{415}(x, y) - 2kA_{416}(x, y)$$

Also, the indicator X (Expression 3) is expressed by Expression 20 below as well.

$$X(x, y) = [A_{R1}(x, y) + A_{R3}(x, y)] / A_{R2}(x, y) \quad \text{Expression 20}$$
$$= [A_{415}(x, y) - kA_{416}(x, y)] / kA_{416}(x, y)$$
$$= \frac{1}{k} \cdot \frac{A_{415}(x, y)}{A_{416}(x, y)} - 1$$

Here, k is a constant (correction coefficient). The optical filters 415 and 416 have pass wavelength regions with very different widths, and the quantity of light that passes through is also very different between them. For this reason, as described above, the light quantity is adjusted by placing the light attenuation filter 419 over the optical filter 415 that has a high light passage rate, such that the same exposure time and appropriate exposure are obtained even if the optical filters are switched. As a result, the quantitative relationship is lost between the absorption $A_{415}(x,y)$ acquired using the optical filter 415 and the absorption $A_{416}(x,y)$ acquired using the optical filter 416. Also, the passage rate is not 100% in the pass wavelength regions of the optical filters 115 and 416, and passage loss is different for individual optical filters. Also, there is error in the pass wavelength regions of the optical filters 415 and 416 as well. For this reason, even if the light attenuation filter 419 is not used, a certain amount of error is included in the quantitative relationship between the absorption $A_{415}(x,y)$ and the absorption $A_{416}(xy)$. The correction coefficient k is for correcting error in the quantitative relationship between the absorption $A_{415}(x,y)$ and the absorption $A_{416}(x,y)$. A method for acquiring the correction coefficient k will be described later. Note that in the case of not performing this correction, the correction coefficient k is set to 1.

Furthermore, if Expression 19 is rearranged using Expressions 9 and 10 and Expressions 7 and 8, then Expression 21 below is obtained.

$$X(x, y) = -\log[SR_{415}(x, y)] + 2k\log[SR_{416}(x, y)] \quad \text{Expression 21}$$
$$= -\log\left[\frac{G_{415}(x, y)/BL_{415}(x, y)}{R_{417}(x, y)/BL_{417}(x, y)}\right] +$$
$$2k\log\left[\frac{G_{416}(x, y)/BL_{416}(x, y)}{R_{417}(x, y)/BL_{417}(x, y)}\right]$$
$$= -\left\{\begin{array}{l}[\log G_{415}(x, y) - \log BL_{415}(x, y)] - \\ [\log R_{417}(x, y) - \log BL_{417}(x, y)] -\end{array}\right\} +$$
$$2k\left\{\begin{array}{l}[\log G_{416}(x, y) - \log BL_{416}(x, y)] - \\ [\log R_{417}(x, y) - \log BL_{417}(x, y)] -\end{array}\right\}$$
$$= -[\log G_{415}(x, y) - \log BL_{415}(x, y)] +$$
$$2k[\log G_{416}(x, y) - \log BL_{416}(x, y)] +$$
$$(1 - 2k)[\log R_{417}(x, y) - \log BL_{417}(x, y)]$$

Accordingly, by using Expression 21, it is possible to calculate the value of the indicator X from the G digital image data $G_{415}(x,y)$ and $G_{416}(x,y)$, the R digital image data $R_{417}(x,y)$, and the baseline image data $BL_{415}(x,y)$, $BL_{416}(x,y)$, and $BL_{417}(x,y)$ (processing S6).

Also, the indicator X can be approximately obtained using Expression 22 below as well.

$$X(x, y) = -\log[SR_{415}(x, y)] + 2k \log[SR_{416}(x, y)] \approx -SR_{415}(x, y) + 2kSR_{416}(x, y) \quad \text{Expression 22}$$

Next, the image processing unit 500 performs processing S7 (FIG. 5) for acquiring a degree of oxygen saturation $SatO_2(x,y)$ for each pixel (x,y) based on the indicator X (x,y) acquired in processing S6. In processing S7, pixels that satisfy a predetermined condition are subjected to processing for acquiring a degree of oxygen saturation $SatO_2(x,y)$ in which error arising from scattering has been corrected, and pixels that do not satisfy the predetermined condition (i.e., have the possibility of instead reducing the precision of the analysis results due to correction) are subjected to processing for acquiring an uncorrected degree of oxygen saturation $SatO_2(x,y)$ that includes error arising from scattering.

Before describing the specific procedure of processing S7, the following describes error arising from scattering that is included in the indicator X.

Figure 6:
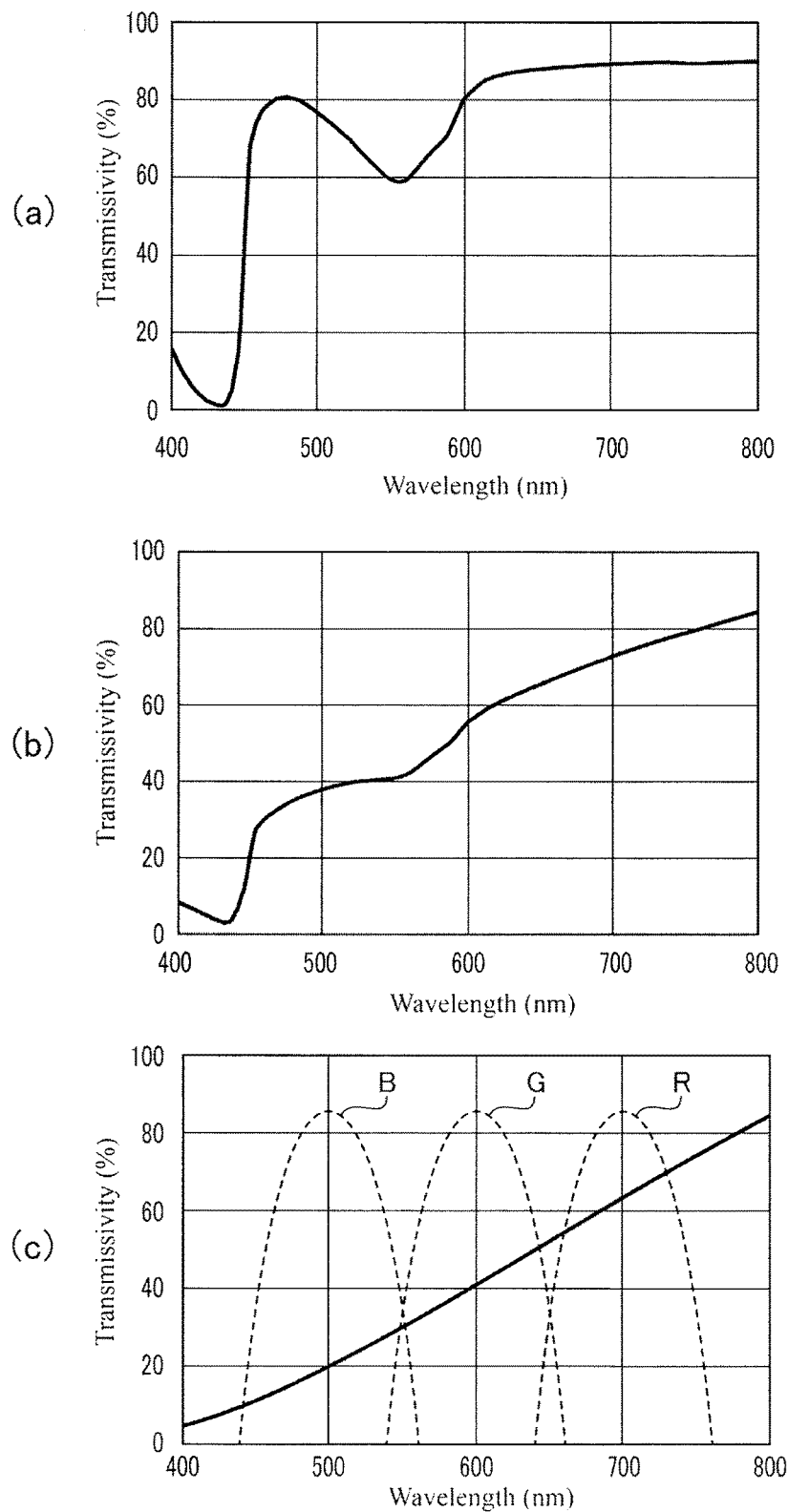
FIG. 6 shows results of simulation of the spectral characteristics of biological tissue in order to describe the influence of scattering on spectral characteristics.

FIG. 6 shows spectral characteristics (a reflection spectrum) of biological tissue obtained by simulation calculation, and shows the influence of scattering on spectral characteristics. The reflection spectrum of biological tissue such as a digestive track wall is influenced by not only the absorption wavelength characteristics of the components that make up the biological tissue (specifically, the absorption spectrum characteristics of oxygenated hemoglobin $HbO_2$ and reduced hemoglobin Hb), but also the scattering wavelength characteristics thereof. FIG. 6(a) shows the reflection spectrum in the case of no scattering whatsoever (the case where the scattering contribution rate C is 0%). FIG. 6(c) shows the reflection spectrum in the case where there is no absorption whatsoever by hemoglobin (the case where the scattering contribution rate C is 100%), and FIG. 6(b) shows the reflection spectrum in the case where the extents of the contribution of scattering and the contribution of hemoglobin absorption on the reflection spectrum are the same (the case where the scattering contribution rate C is 50%). The reflection spectrum of the biological tissue is assumed to be close to that in FIG. 6(b). Here, the scattering contribution rate C is one type of parameter that indicates the extent of contribution (contribution) of scattering in the spectral characteristics of the biological tissue. The contribution of scattering is a parameter that is correlated with the concentration on the scatterer and is used in spectral characteristics simulation calculation, and is multiplied with the scatter term. The scattering contribution rate C in the present embodiment is a parameter that indicates the percentage of the component arising from scattering in the spectral characteristics of the biological tissue.

As shown in FIG. 6, the biological tissue spectral characteristics vary according to the intensity of scattering (contribution rate C), and therefore the indicator X calculated based on the biological tissue spectral characteristics can also change in value according to the intensity of scattering. In other words, the indicator X calculated in processing S6 includes error arising from scattering. In order to obtain a more precise analysis result, it is necessary to correct the error arising from scattering.

As shown in FIG. 6(c), the scattering spectral characteristics exhibit a waveform that monotonically increases relative to the wavelength. For this reason, the amounts of scattered light that pass through the B, G, and R, filters of the image sensor 141 (the transmission spectrums of the filters are schematically shown by dashed lines in FIG. 6(c)) increase in this order, and the ratios therebetween (e.g., the ratio of the amount of scattered light that passes through the R filter to the amount of scattered light that passes through the G filter) are approximately constant regardless of the intensity of scattering. Also, the representative example of the reflection spectrum of biological tissue indicated in FIG. 6(b) also has a waveform that gently increases along with the wavelength and resembles the spectrum of scattered light in FIG. 6(c) when viewed over a long wavelength range. The slope of the reflection spectrum of biological tissue decreases (approaches the inclination of the waveform in FIG. 6(a)) as scattering decreases, and increases (approaches the inclination of the waveform in FIG. 6(c)) as scattering increases. For this reason, the intensity of scattering can be estimated based on the ratio of the amounts of light that pass through two different color filters, such as the ratio between the transmitted light amount of the G filter (value of G digital image data) and the transmitted light amount of the R filter (value of R digital image data).

Figure 7:
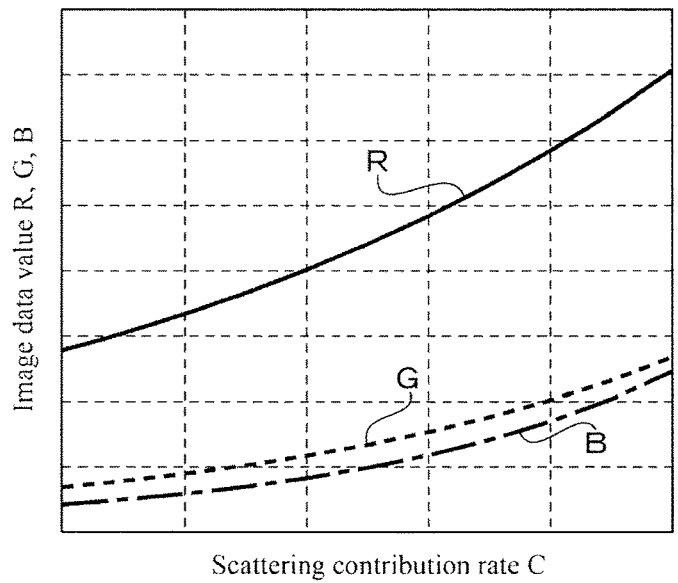
FIG. 7 is a graph showing the relationship between a scattering contribution rate C and R, G, and B digital image data acquired under white light illumination.

FIG. 7 is a graph showing the relationship between the scattering contribution rate C and the values of R digital image data $R_{418}$, G digital image data $G_{418}$, and B digital image data $B_{418}$, which was obtained by simulation calculation performed based on experimental values. According to FIG. 7, sensitivity to the scattering contribution rate C (the inclination in the graph in FIG. 7) is the highest with the R digital image data $R_{418}$ and the lowest with the G digital image data $G_{418}$. Accordingly, a standardized value obtained by dividing the R digital image data $R_{418}$ by the G digital image data $G_{418}$ is a good indicator of the scattering contribution rate C. In view of this, in the present embodiment, the scattering contribution rate C is calculated using Expression 23 below.

$$C(x, y) = R_{418}(x, y)/G_{418}(x, y) \quad \text{Expression 23}$$

Note that the sensitivity of the B digital image data $B_{418}$ to the scattering contribution rate C also is not largely different from the sensitivity of the G digital image data $G_{418}$, and therefore a value obtained by dividing the R digital image data $R_{418}$ by the B digital image data $B_{418}$ can also be used as the contribution rate C.

Figure 8:
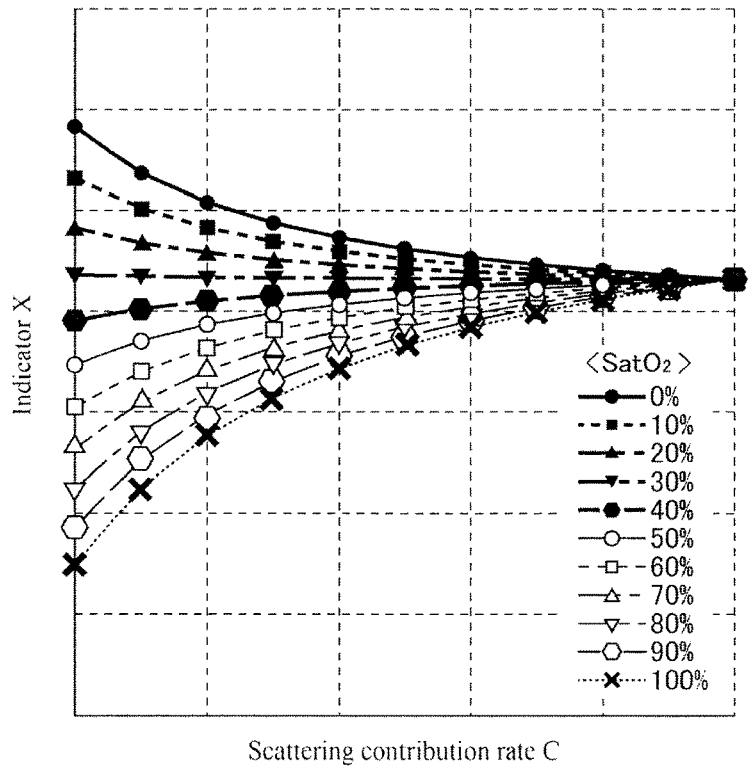
FIG. 8 is a graph in which the relationship between the scattering contribution rate C and an indicator X is plotted for each real degree of oxygen saturation $SatO_2$.

FIG. 8 is a graph in which the relationship between the scattering contribution rate C and the indicator X calculated in processing S5 (FIG. 5) is plotted for each real (i.e., not including error arising from scattering) degree of oxygen saturation $SatO_2$. The quantitative relationship shown in FIG. 8 can be acquired by simulation calculation or experimentation. In the graph in FIG. 8, by selecting the curve that is closest to the plotted point of the set of the indicator X obtained based on biological tissue image data and the scattering contribution rate C, and then acquiring the degree of oxygen saturation $SatO_2$ that corresponds to the selected curve, it is possible to obtain an approximate value for the degree of oxygen saturation $SatO_2$ in which error arising from scattering has been corrected.

In the present embodiment, the quantitative relationship shown in FIG. 8 is acquired in advance by simulation calculation or experimentation, and is held as a numerical value table, a function, or the like in the non-volatile memory 532 of the controller 530.

Next, the specific procedure of processing S7 will be described.

Figure 9:
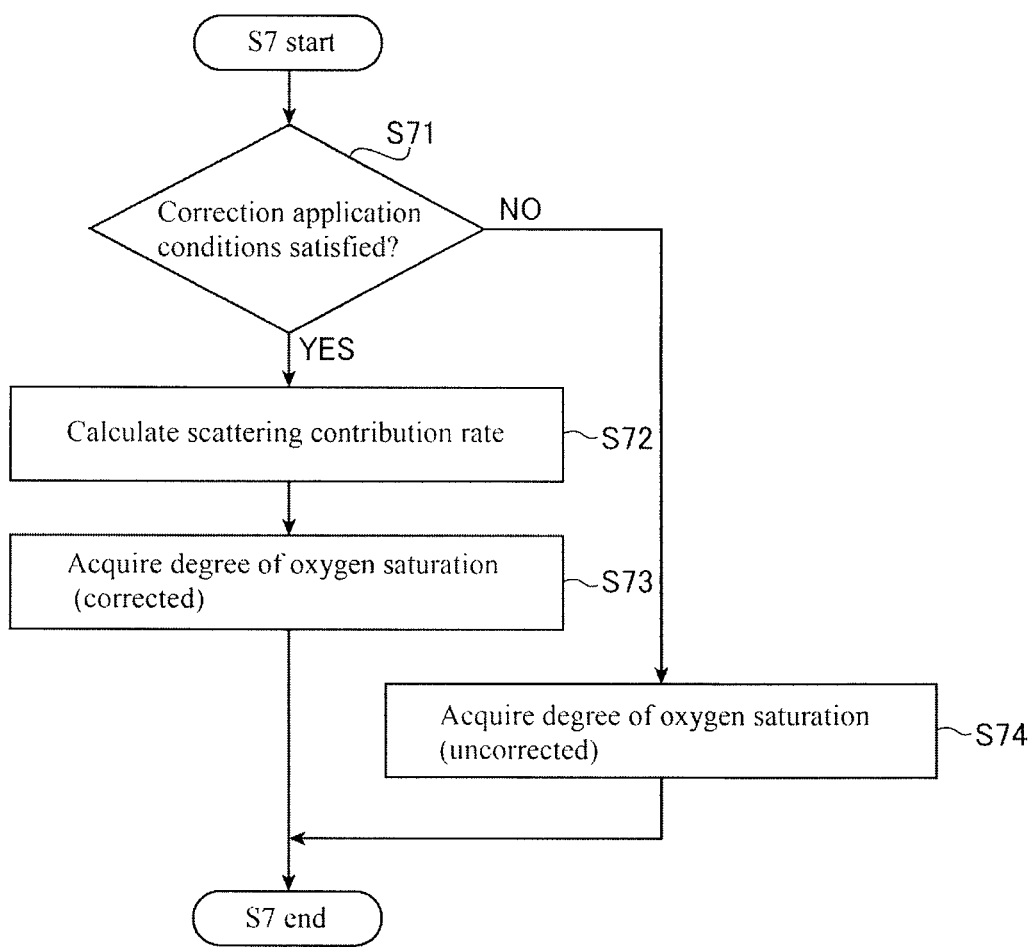
FIG. 9 is a flowchart showing a procedure of processing for acquiring the degree of oxygen saturation $SatO_2$ based on the indicator X.

FIG. 9 is a flowchart showing the procedure of degree of oxygen saturation acquisition processing (feature amount acquisition processing) S7.

In processing S7, first, it, is determined whether or not the values of the R digital image data $R_{418}$, the G digital image data $G_{418}$, and the B digital image data $B_{418}$ are suited to the correction of error arising from scattering (processing S71). Specifically, it is determined whether or not the two conditional expressions shown in Expressions 24 and 25 below hold true.

$$b_1 < C(x, y) = R_{418}(x, y)/G_{418}(x, y) < b_2 \quad \text{Expression 24}$$

$$R_{418}(x, y) + G_{418}(x, y) + B_{418}(x, y) > b_3 \quad \text{Expression 25}$$

Here, $b_1$, $b_2$, and $b_3$ are threshold values (positive constants).

If the contribution rate C is too small or conversely too large, it is determined that the reliability of the R digital image data $R_{418}$ or the G digital image data $G_{418}$ is low, and therefore Expression 24 is for excluding such data from being subjected to scattering correction based on the contribution rate C.

Also, if the image is dark, it is determined that the reliability of all of the pixel values (R digital image data $R_{418}$ and G digital image data $G_{418}$) is low, and therefore. Expression 25 is for defining a lower limit of brightness. Note that instead of using Expression 25, it is possible to, for example, use only the G digital image data $G_{418}$ and set the lower limit of brightness using Expression 26 below.

$$G_{418}(x, y) > b'_3 \quad \text{Expression 26}$$

Here, $b_3'$ is a threshold value (positive constant).

If the two conditions of Expressions 24 and 25 (or 26) both hold true (S71:YES), the procedure moves to processing S72-73, and a degree of oxygen saturation $SatO_2$ that has been corrected for the influence of scattering is acquired. Also, even if one of the conditions does not hold true (S71:NO), the procedure moves to processing S74, and an uncorrected degree of oxygen saturation $SatO_2$ that includes error arising from scattering is acquired.

In processing S72, Expression 23 described above is used to calculate the contribution rate C(x,y) for each pixel (x,y).

In processing S73, the quantitative relationship shown in FIG. 8 is used to acquire a degree of oxygen saturation SatO$_2$(x,y) of hemoglobin that has been corrected for error arising from scattering, based on the scattering contribution rate C(x,y) obtained in processing S72 and the indicator X(x,y) obtained in processing S5. Specifically, the pair (C,X) of the scattering contribution rate C(x,y) obtained in processing S72 and the indicator X(x,y) obtained in processing S5 is plotted on the graph in FIG. 8, the curve that is closest to the plotted point (C,X) is selected, and the degree of oxygen saturation SatO$_2$(x,y) that corresponds to the selected curve is acquired as the degree of oxygen saturation SatO$_2$(x,y) at that pixel (x,y).

Note that in processing S73 of the present embodiment the degree of oxygen saturation SatO$_2$ that corresponds to the curve that is closest to the plotted point (C,X) on the graph in FIG. 8 is acquired as described above, but the present invention is not limited to this configuration. For example, it is possible to select a pair of curves that are adjacent to the point (C,X) (i.e., sandwich the point (C,X)) on the graph in FIG. 8, calculate a weighted average of the degrees of oxygen saturation SatO$_2$ that correspond to the curves using weights that correspond to the distance between the point (C,X) and the curves, and acquire the weighted average value as the degree of oxygen saturation SatO$_2$ at the pixel (x,y).

Figure 10:
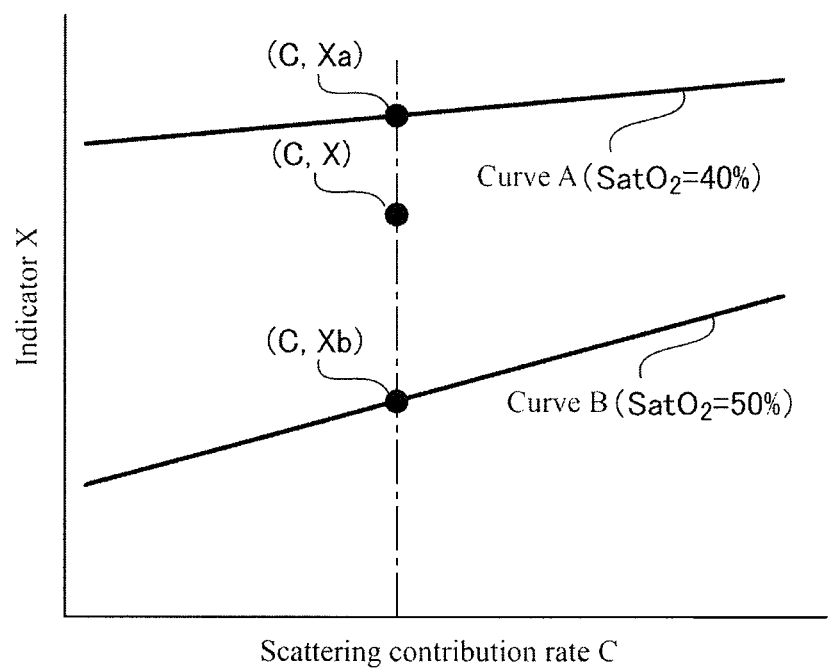
FIG. 10 is a diagram illustrating a method of acquiring the degree of oxygen saturation $SatO_2$ by weighted averaging with use of the graph of FIG. 8.

The following describes a specific example of a method of acquiring the degree of oxygen saturation SatO$_2$ by weighted averaging with reference to FIG. 10. In the example in FIG. 10, the point (C,X) obtained by analysis processing is located between a curve A indicating the relationship between the contribution rate C and the indicator X when the degree of oxygen saturation SatO$_2$ is 40% and a curve B when the degree of oxygen saturation SatO$_2$ is 50%. At the contribution rate C, when the indicator on the curve A is Xa and the indicator on the curve B is Xb, the degree of oxygen saturation SatO$_2$ that corresponds to the point (C,X) (corrected for error arising from scattering) is calculated by the weighted averaging of Expression 27 below.

$$SatO_2 = \frac{X - Xb}{Xa - Xb} \cdot [SatO_2]_a + \frac{Xa - X}{Xa - Xb} \cdot [SatO_2]_b \quad \text{Expression 27}$$
$$= \frac{X - Xb}{Xa - Xb} \cdot 40\% + \frac{Xa - X}{Xa - Xb} \cdot 50\%$$

Here, [SatO$_2$]$_a$ is the degree of oxygen saturation SatO$_2$ (40%) that corresponds to the curve A, and [SatO$_2$]$_b$ is the degree of oxygen saturation SatO$_2$ (50%) that corresponds to the curve B.

Also, the non-volatile memory 532 of the controller 530 stores a numerical value table (or function) that has been acquired by experimentation in advance and expresses the quantitative relationship between the degree of oxygen saturation SatO$_2$ of hemoglobin and the value of the indicator X with no consideration given to the influence of scattering. In processing S74, the controller 530 references this numerical value table (or function), and acquires the degree of oxygen saturation SatO$_2$(x,y) that corresponds to the value of the indicator X obtained in processing S5.

The non-volatile memory 532 of the controller 530 stores a numerical value table (or function) that expresses the relationship between the degree of oxygen saturation SatO$_2$(x,y) and display colors (pixel values). Then, in processing S8 (FIG. 5), the controller 530 references this numerical value table (or function), and acquires the pixel value that indicates the display color corresponding to the degree of oxygen saturation SatO$_2$(x,y) obtained in processing S7.

The controller 530 then generates normal observation image data based on the R digital image data R$_{418}$(x,y), the G digital image data G$_{418}$(x,y), and the B digital image data B$_{418}$(x,y) that were obtained using illumination light IL (white light) that passes through the optical filter (ultraviolet cut filter) 418.

Figure 11:
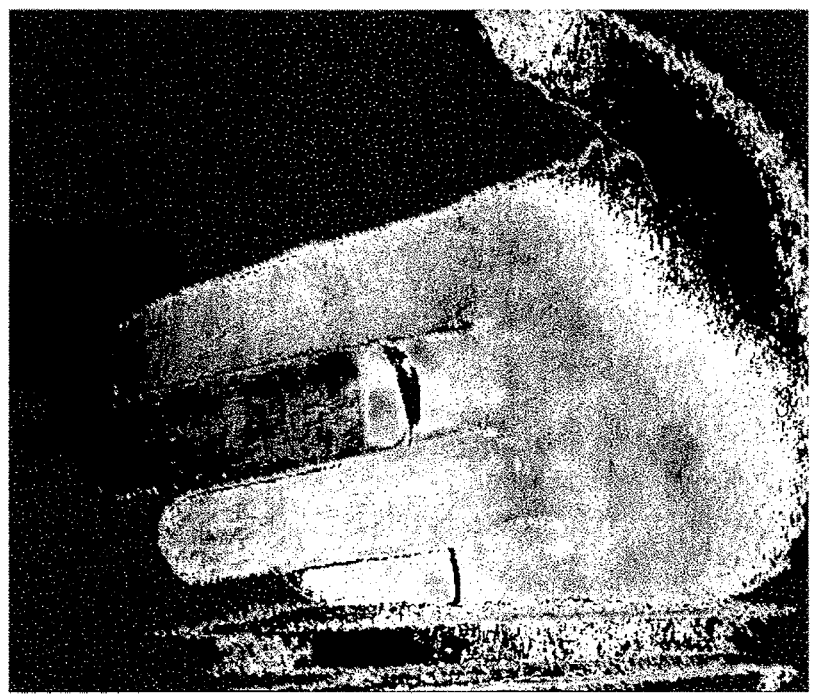
FIG. 11 shows an example of display of image information generated by the endoscope apparatus according to the embodiment of the present invention. (a) shows an example of two-dimensional display of a degree of oxygen saturation distribution image and (b) shows an example of three-dimensional display of a degree of oxygen saturation distribution image.
Figure 11:
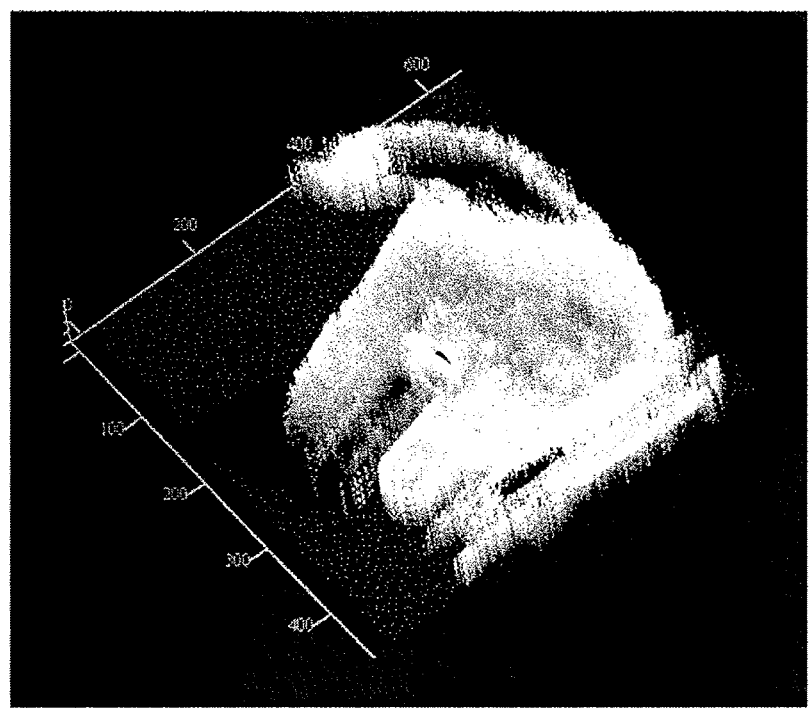

FIG. 11 shows an example of the display of image data generated by the controller 530. FIG. 11(a) is an example of the display of degree of oxygen saturation distribution image data (two-dimensional display) generated by processing S8 described above. Also, FIG. 11(b) is an example of the display of degree of oxygen saturation distribution image data (three-dimensional display) generated in a three-dimensional graph format in which the degree of oxygen saturation SatO$_2$ is the vertical axis. Note that FIG. 11 shows the observation of a right hand in the state where an elastic band constricts the vicinity of the proximal interphalangeal joint of the middle finger. On the distal side of the constricted site of the right middle finger, the flow of blood is inhibited by the constriction, and therefore it is seen that the degree of oxygen saturation SatO$_2$ is low.

The controller 530 then uses the generated degree of oxygen saturation distribution image data and normal observation image data to generate screen data in which the normal observation image and the degree of oxygen saturation distribution image are displayed side-by-side in one screen, and stores the screen data in the video memory 540. Note that in accordance with a user operation, the controller 530 can generate various types of display screens, such as a display screen that displays only the degree of oxygen saturation distribution image, a display screen that displays only the normal observation image, or a display screen that displays supplementary information such as patient ID information and observation conditions in a superimposed manner on the degree of oxygen saturation distribution image and/or the normal observation image.

Next, a method of determining the correction coefficient k in the calibration mode will be described. In the present embodiment, theoretical calculation values and measured values of the indicator X are compared, and the value of the correction coefficient k is determined such that the actual measured values come closest to the theoretical calculation values.

Figure 12:
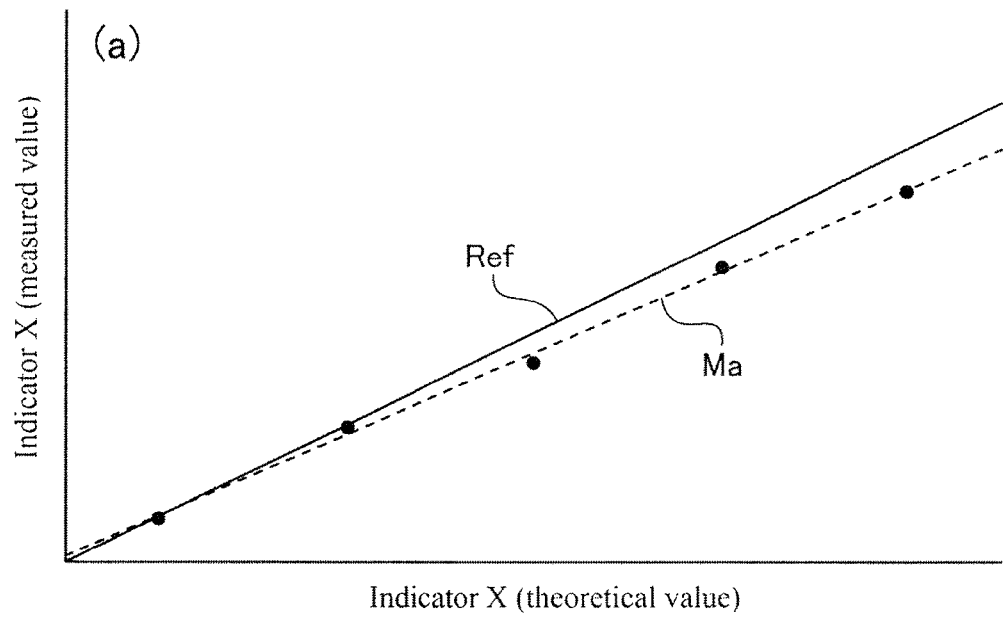
FIG. 12 shows examples of a calibration curve used when determining a correction coefficient k.
Figure 12:
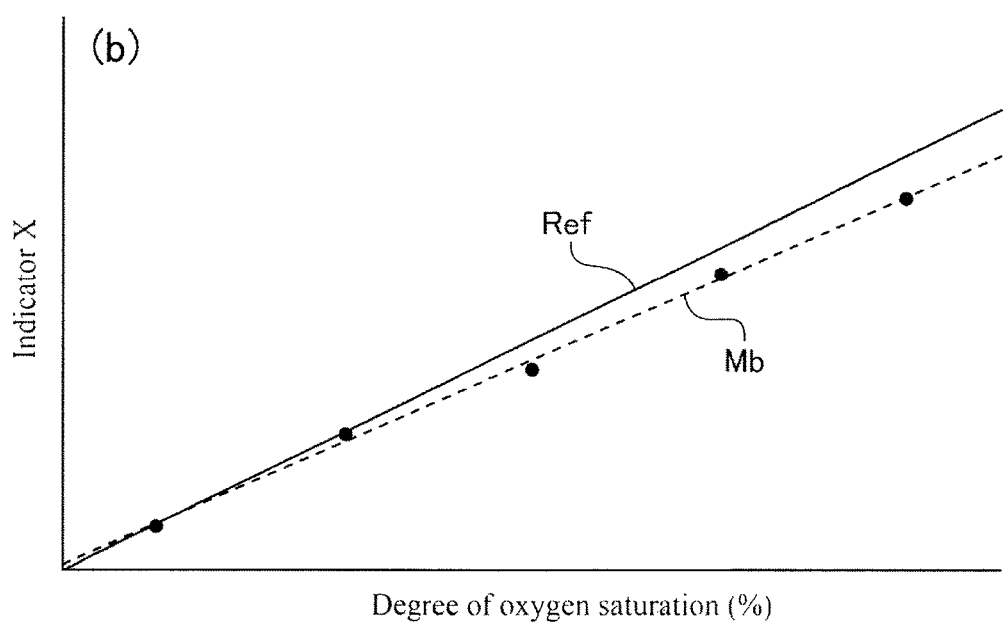

FIG. 12 shows examples of a calibration curve used when determining the correction coefficient; k in this embodiment of the present invention. FIG. 12(a) shows an example of a general calibration curve, where the theoretical value of the indicator X is indicated on the horizontal axis, and the measured value of the indicator X acquired by the above-described analysis processing is indicated on the vertical axis. Black circles are plotted points for the measured value, and the dashed line Ma is a straight line fitted to the measured values by the least squares method. Also, the solid line indicates a reference line Ref plotted when measured values are obtained according to theoretical values.

A measured value of the indicator X is acquired by the analysis processing using a sample of biological tissue (e.g., blood) that has a known degree of oxygen saturation SatO$_2$. Also, a theoretical value of the indicator X defined by Expression 19 is calculated using the transmission spectrum of the optical filters 415 and 416 that are actually used, and the reflection spectrum (or absorption spectrum) of blood. Specifically, letting the absorption A$_{415}$ (absorption A$_{416}$) be the cumulative product of the transmission spectrum of the optical filter 415 (optical filter 416) and the reflection spectrum of blood for example, the theoretical value of the indicator X is calculated using Expression 19.

Deviation between the reference line Ref and the measured value Ma is expressed as the inclination of the dashed line Ma relative to the reference line Ref. The phenomenon in which sufficient sensitivity is not obtained, that is to say the phenomenon in which the gradient of the dashed line Ma is gentle, arises from the loss of the quantitative relationship between the absorption $A_{415}(x,y)$ and the absorption $A_{416}(x,y)$ in Expression 19 due to using the light attenuation filter 419. By selecting an appropriate value for the correction coefficient k, error arising from use of the light attenuation filter 419 is corrected, and it is possible to achieve a state in which the measured value of the indicator X has little error and a high correlation with the theoretical value.

FIG. 12(b) shows a variation of the calibration curve. With the calibration curve in FIG. 12(b), the degree of oxygen saturation of a sample is indicated on the horizontal axis, and the indicator X is indicated on the vertical axis. Black circles are plotted points for the measured value, and a dashed line Mb is a straight line fitted to the measured values by the least squares method. Also, the solid line Ref indicates theoretical calculation values. Note that the degrees of oxygen saturation of the sample are values accurately measured by ideal spectrometry. This calibration curve is obtained by changing the scale of the horizontal axis from that of the calibration curve in FIG. 12(a), and although substantially equivalent, it has the advantage of facilitating understanding of the relationship with the value of the degree of oxygen saturation.

Note that this method of determining the correction coefficient k with use of the above-described calibration curve uses the analysis results of multiple samples that have different degrees of oxygen saturation $SatO_2$, but the correction coefficient k may be determined using the analysis results of only one sample.

Also, when focus is placed on the hemoglobin absorption wavelength regions R1, R2, and R3 (i.e., the pass wavelength region of the optical filter 415), the absorptions $A_{R1}(x,y)$, $A_{R2}(x,y)$, and $A_{R3}(x,y)$ in the wavelength regions R1, R2, and R3 vary according to change in the degree of oxygen saturation $SatO_2$, but a sum Y of these absorptions (shown in Expression 28) is approximately constant. Also, this sum Y of the absorptions is proportional to the total hemoglobin amount in the biological tissue (sum of the concentrations of oxygenated hemoglobin $HbO_2$ and reduced hemoglobin Hb), and therefore it is reasonable to use this sum as an indicator that indicates the total hemoglobin amount.

$$Y(x, y) = A_{R1}(x, y) + A_{R2}(x, y) + A_{R3}(x, y) = A_{415} \qquad \text{Expression 28}$$

Note that similarly to processing S7 described above, a numerical value table or a function can be used to acquire the value of the total hemoglobin amount from the indicator Y. Also, similarly to processing S72-73, the value of the total hemoglobin amount corrected for the influence of scattering can also be obtained based on the scattering contribution rate C.

Malignant tumor tissue has a higher total hemoglobin amount than normal tissue due to angiogenesis, and also exhibits remarkable oxygen metabolism, and therefore it is known that the degree of oxygen saturation $SatO_2$ is lower than that of normal tissue. In view of this, the controller 530 can extract the pixels for which the indicator Y, which was calculated using Expression 28 and indicates the total hemoglobin amount is greater than a predetermined reference value (first reference value), and for which the indicator X, which was calculated using Expression 19 or the like and indicates the degree of oxygen saturation $SatO_2$, is less than a predetermined reference value (second reference value), perform enhanced display processing on corresponding pixels of normal observation image data for example to generate enhanced lesion site image data, and display the enhanced lesion site image on the monitor 300 along with the normal observation image and/or the degree of oxygen saturation distribution image (or on its own).

Examples of enhanced display processing include processing for increasing the pixel values of corresponding pixels, processing for changing the hue (e.g., processing for increasing the redness by increasing the R component, or processing for rotating the hue by a predetermined angle), and processing for flashing corresponding pixels (or periodically changing the hue). Also, processing that combines two or more of the above may be performed.

Also, a configuration is possible in which, instead of generating enhanced lesion site image data, the controller 530 calculates an indicator $Z(x,y)$ that indicates the degree of suspicion of a malignant tumor based on the deviation of the indicator $X(x,y)$ from an average value and the deviation of the indicator $Y(x,y)$ from an average value, and generate image data in which the pixel values are the indicator Z (malignancy suspicion image data).

First Variation

Next, a first variation of the above-described embodiment of the present invention will be described.

In the embodiment described above, the indicator X is calculated by adding the absorptions $A_{R1}$, $A_{R2}$, and $A_{R3}$ in the wavelength regions R1, R2, and R3 without weighting (note that the signs were adjusted so as to align the increase/decrease in the wavelength regions), as shown in Expression 2. In contrast, in the present variation, when the indicator X is calculated, the absorptions $A_{R1}$, $A_{R2}$, and $A_{R3}$ in the wavelength regions are weighted so as to improve the sensitivity of the indicator X with respect to change in the degree of oxygen saturation $SatO_2$.

As shown in FIG. 1, in the wavelength region R2, the variation range of absorbance relative to change in the degree of oxygen saturation $SatO_2$ is greater than in the wavelength regions R1 and R3. For this reason, by setting a higher weight for the absorption $A_{R2}$ in the wavelength region R2 it is possible to improve the sensitivity of the indicator X to change in the degree of oxygen saturation $SatO_2$.

Specifically, the absorption $A_{R2}$ is weighted with a factor of 2, and the indicator X is calculated using Expression 29 below.

$$\begin{aligned}
X(x, y) &= [A_{R1}(x, y) + A_{R3}(x, y)] - 2 \times A_{R2}(x, y) \qquad \text{Expression 29}\\
&= [A_{415}(x, y) - kA_{416}(x, y)] - 2kA_{416}(x, y)\\
&= A_{415}(x, y) - 3kA_{416}(x, y)\\
&= -\log[SR_{415}(x, y)] + 3k\log[SR_{416}(x, y)]\\
&= -\log\left[\frac{G_{415}(x, y)/BL_{415}(x, y)}{R_{417}(x, y)/BL_{417}(x, y)}\right] +\\
&\quad 3k\log\left[\frac{G_{416}(x, y)/BL_{416}(x, y)}{R_{417}(x, y)/BL_{417}(x, y)}\right]\\
&= -\left\{\begin{array}{l}[\log G_{415}(x, y) - \log BL_{415}(x, y)] -\\ [\log R_{417}(x, y) - \log BL_{417}(x, y)]\end{array}\right\} +\\
&\quad 3k\left\{\begin{array}{l}[\log G_{416}(x, y) - \log BL_{416}(x, y)] -\\ [\log R_{417}(x, y) - \log BL_{417}(x, y)] -\end{array}\right\}\\
&= -[\log G_{415}(x, y) - \log BL_{415}(x, y)] +
\end{aligned}$$

-continued $$3k[\log G_{416}(x, y) - \log BL_{416}(x, y)] +$$
$$(1 - 3k)[\log R_{417}(x, y) - \log BL_{417}(x, y)]$$

Also, the indicator X can be approximately obtained using Expression 30 below as well.

$$X(x, y) = -\log[SR_{415}(x, y)] + 3k \log[SR_{416}(x, y)] \cong -SR_{415}(x, y) + 3kSR_{416}(x, y) \quad \text{Expression 30}$$

Note that although the ratio of the weight of the absorption $A_{R2}$ is a factor of 2 relative to the absorptions $A_{R1}$ and $A_{R3}$ in the first variation described above, this ratio can be appropriately changed to another value (e.g., a factor of 1.5 or 2.4) so as to obtain a suitable sensitivity and amount of noise. Also, by generalizing Expression 29, letting w1 be the weight of the absorptions $A_{R1}$ and $A_{R3}$, and letting w2 be the weight of the absorption $A_{R2}$, the indicator X can be described using Expression 31.

$$X(x, y) = w1 \times [A_{R1}(x, y) + A_{R3}(x, y)] - w2 \times A_{R2}(x, y)$$
$$= w1 \cdot [A_{415}(x, y) - kA_{416}(x, y)] - w2 \cdot k \cdot A_{416}(x, y)$$
$$= w1 \cdot A_{415}(x, y) - k \cdot (w1 + w2) \cdot A_{416}(x, y)$$
$$= -w1 \cdot \log[SR_{415}(x, y)] + k \cdot (w1 + w2) \cdot \log[SR_{416}(x, y)]$$

Expression 31

Also, the indicator X can be approximately obtained using Expression 32 below as well.

$$X(x, y) \cong -w1 \cdot SR_{415}(x, y) + k \cdot (w1 + w2) \cdot SR_{416}(x, y) \quad \text{Expression 32}$$

Second Variation

Next, a second variation of the embodiment of the present invention will be described.

In the embodiment described above, the indicator X is calculated based on the difference between the sum of the absorptions $Ar_1$ and $Ar_3$ in the wavelength regions R1 and R3, in which absorption increases along with increase in the degree of oxygen saturation $SatO_2$, and the absorption $A_{R2}$ in the wavelength region R2, in which absorption decreases along with increase in the degree of oxygen saturation $SatO_2$, as shown in Expression 2. In contrast, in the present variation, the indicator X is calculated based on the ratio of the sum of the absorptions $A_{R1}$ and $A_{R3}$ and the absorption $A_{R2}$.

Specifically, the indicator X is calculated using Expression 33 below.

$$X(x, y) = \frac{A_{R1}(x, y) + A_{R3}(x, y)}{A_{R2}(x, y)}$$
$$= \frac{A_{415}(x, y) - kA_{416}(x, y)}{kA_{416}(x, y)}$$
$$= \frac{A_{415}(x, y)}{kA_{416}(x, y)} - 1$$
$$= \frac{\log[SR_{415}(x, y)]}{k\log[SR_{416}(x, y)]} - 1$$

Expression 33

Also, the indicator X can be approximately obtained using Expression 34 below as well.

$$X(x, y) \cong \frac{SR_{415}(x, y)}{kSR_{416}(x, y)} - 1 \quad \text{Expression 34}$$

Also, the indicator X may be calculated using Expression 35 or 36 below, in which the weight w1 is given to the sum $A_{R1}+A_{R3}$ of the absorptions in the wavelength regions R1 and R3, which has a positive correlation with the degree of oxygen saturation $SatO_2$, and the weight w2 is given to the absorption $A_{R2}$ in the wavelength region R2, which has a negative correlation.

$$X(x, y) = \frac{w1 \cdot [A_{R1}(x, y) + A_{R3}(x, y)]}{w2 \cdot [A_{R2}(x, y)]}$$
$$= \frac{w1}{w2} \cdot \frac{A_{415}(x, y) - kA_{416}(x, y)}{k \cdot A_{416}(x, y)}$$
$$= \frac{w1}{w2} \cdot \left[\frac{A_{415}(x, y)}{kA_{416}(x, y)} - 1\right]$$
$$= \frac{w1}{w2} \cdot \left\{\frac{\log[SR_{415}(x, y)]}{k\log[SR_{416}(x, y)]} - 1\right\}$$

Expression 35

$$X(x, y) = \frac{[A_{R1}(x, y) + A_{R3}(x, y)]^{w1}}{[A_{R2}(x, y)]^{w2}}$$
$$= \frac{[A_{415}(x, y) - kA_{416}(x, y)]^{w1}}{[kA_{416}(x, y)]^{w2}}$$
$$= \frac{\{-\log[SR_{415}(x, y)] + k\log[SR_{416}(x, y)]\}^{w1}}{[kA_{416}(x, y)]^{w2}}$$

Expression 36

Also, the absorptions $A_{R1}$ and $A_{R3}$ in the wavelength regions R1 and R3 are proportional to the concentration of oxygenated hemoglobin $HbO_2$ the degree of oxygen saturation $SatO_2$), and the absorption $A_{R2}$ in the wavelength region R2 is proportional to the concentration of reduced hemoglobin Hb (i.e., 1-$SatO_2$), and therefore Expression 37 below is obtained from the first line of Expression 33.

$$X(x, y) = \frac{A_{R1}(x, y) + A_{R3}(x, y)}{A_{R2}(x, y)} \propto \frac{D_{Sat}(x, y)}{1 - D_{Sat}(x, y)} \quad \text{Expression 37}$$

Here, $D_{Sat}(x,y)$ is the degree of oxygen saturation $SatO_2$ at the pixel (x,y).

Accordingly, the indicator X calculated using Expression 37 increases exponentially as $D_{Sat}(x,y)$ (degree of oxygen saturation $SatO_2$) increases and approaches 1, and therefore this indicator X is a good indicator for sensitivity.

Third Variation

Next, a third variation of the embodiment of the present invention will be described.

In the embodiment described above, in second standardization processing S4, processing is performed for division by the R digital image data $R_{417}(x,y)$ obtained using illumination light IL in the 650 nm band that passes through the optical filter 417, but the present invention is not limited to this configuration. For example, a configuration can be employed in which in the second standardization processing, division is performed by the sum of R, G, and B digital image data obtained using illumination light IL that passes through the optical filter 418 (or an light attenuation filter that has no wavelength dependency, or a simple transparent window).

In this case, standardization reflectances $SR_{415}(x,y)$ and $SR_{416}(x,y)$ are calculated using Expressions 38 and 39 respectively.

$$SR_{415}(x, y) = \frac{G_{415}(x, y) / BL_{415}(x, y)}{\frac{R_{418}(x, y)}{BL_{R418}(x, y)} + \frac{G_{418}(x, y)}{BL_{G418}(x, y)} + \frac{B_{418}(x, y)}{BL_{B418}(x, y)}} \quad \text{Expression 38}$$

$$SR_{416}(x, y) = \frac{G_{416}(x, y)/BL_{416}(x, y)}{\frac{R_{418}(x, y)}{BL_{R418}(x, y)} + \frac{G_{418}(x, y)}{BL_{G418}(x, y)} + \frac{B_{418}(x, y)}{BL_{B418}(x, y)}}$$ Expression 39

Here, baseline image data $BL_{R418}(x,y)$, $BL_{G418}(x,y)$, and $BL_{B418}(x,y)$ are R digital image data $R_{418}(x,y)$, G digital image data $G_{418}(x,y)$, and B digital image data $B_{418}(x,y)$ obtained by capturing an image of a color reference board illuminated by illumination light. IL that passes through the optical filter 418.

Although an embodiment of the present invention has been described above, the present invention is not limited to the above configuration, and various modifications can be made within the scope of the technical idea of the present invention.

In the above embodiment, the contribution rate C that is calculated expresses the extent of influence (contribution) of scattering on the spectral characteristics of biological tissue as a percentage, but the present invention is not limited to this configuration, and another indicator that expresses the degree of contribution of scattering (e.g., an integer value from 1 to 5 expressing five levels) may be used.

Also, in the above embodiment, a degree of oxygen saturation $SatO_2$ (or total hemoglobin amount) that does not include error arising from scattering (strictly speaking, in which such error has been reduced) is acquired based on the indicator X (or the indicator Y) and the scattering contribution rate C, but the indicator X (or the indicator Y) can be corrected based on the scattering contribution rate C.

Also, in the above embodiment, the scattering contribution rate C is calculated based on single-color image data for two colors, namely the R digital image data $R_{418}(x,y)$ and the C digital image data $G_{418}(xy)$, or the R digital image data $R_{418}(x,y)$ and the B digital image data $B_{418}(x,y)$, but the present invention is not limited to this configuration. For example, a configuration is possible in which the contribution rate C is calculated based on single-color image data for three colors, namely the R digital image data $R_{418}(x,y)$, the C digital image data $G_{418}(x,y)$, and the B digital image data $B_{418}(x,y)$, using the least squares method or weighted average calculation for example. Also, the contribution rate C may be calculated based on only the R digital image data $R_{418}(x,y)$ for example.

Also, in the above embodiment:, the present invention is applied to the analysis of the concentration distribution of hemoglobin in biological tissue, but the present invention can also be applied to the analysis of the concentration distribution of another biological substance (e.g., a secretion such as a hormone) that changes the color of biological tissue.

Also, in the above embodiment, the expressions used to acquire the indicator X of the degree of oxygen saturation $SatO_2$ and the indicator Y of the total hemoglobin amount are examples, and a configuration is possible in which these indicators are acquired using another calculation procedure or method.

Also, in the above embodiment, the value of the degree of oxygen saturation $SatO_2$ is acquired based on the value of the indicator X with use of a numerical value table or a function, and then multiplied by a predetermined constant to calculate a pixel value of a degree of oxygen saturation distribution image, but the present invention is not limited to this configuration. The indicator X is a numerical value that monotonically increases relative to the degree of oxygen saturation $SatO_2$, and therefore the value of the indicator X can be used as is (or after being multiplied by the predetermined constant) as the pixel value of the degree of oxygen saturation distribution image.

Also, the image sensor 141 of the present embodiment is described as an image sensor for color image capturing that, includes R, G, and B primary-color color filters on the front side, but the present invention is not limited to this configuration, and an image sensor for color image capturing that includes Y, Cy, Mg, and G complementary-color color filters for example may be used.

Also, the image sensor 141 of the present embodiment is described as an image sensor for color image capturing that includes an on-chip color filter 141a, but the present invention is not limited to this configuration and a configuration is possible in which for example, an image sensor for black-and-white image capturing is used and includes a so-called frame sequential color filter. Also, the color filter 141a -is not limited to having an on-chip configuration, and can be arranged in the optical path between the light source 430 and the image sensor 141.

Also, although the rotating filter 410 is used in the above embodiment, the present invention is not limited to this configuration, and another type of variable wavelength filter that enables switching the pass wavelength region may be used.

Also, in the above embodiment, a configuration is applied in which the rotating filter 410 is provided on the light source side and performs filtering on irradiation light IL but, the present invention is not limited to this configuration, and a configuration is possible in which the rotating filter 410 is provided on the image sensor side (e.g., between the objective optical system 121 and the image sensor 131) and performs filtering on returning light from the subject.

Also, in the above embodiment, a configuration is applied in which in the spectral analysis mode, images are captured at a predetermined time interval while rotating the rotating filter 410 at a constant rotational frequency, but the present invention is not limited to this configuration, and a configuration is possible in which, for example, the rotation position of the rotating filter 410 is changed in a stepwise manner at a predetermined time interval, and images are captured while the rotating filter 410 is in the stopped state.

Also, in the above embodiment, a white light source such as a xenon lamp is used as the light source that generates wide band light for illumination, but it is possible to use a light source that generates non-white wide band light having a sufficient light quantity over the entire pass wavelength region of the optical filters that are used.

Also, it is possible to, for example, provide primary color light sources that respectively generate light in the R, G, and B wavelength regions, and use a combination of the light generated by the primary color light sources as the white light WL. In this case, a narrow band light source such as a laser can be used for the light sources other than the G primary color light source. Also, a light source that generates wide band light having a sufficient light quantity over the entirety of at least the first illumination wavelength region (the wavelength region R0 shown in FIG. 1) is used as the G primary color light source.

Also, in the above embodiment, the pass wavelength region R0 of the optical filter 415 includes three peak wavelengths, namely the absorption peaks P1 P2, and P3, but a configuration is possible in which the first illumination wavelength region includes only two adjacent absorption peaks (specifically, the absorption peaks P1 and P2, or the absorption peaks P2 and P3).

Also, although transmissive optical filters are used in the above embodiment, reflective optical filters that reflect a pass wavelength region may be used.

Also, although the above embodiment is an example of applying the present invention to an electronic endoscope apparatus that is one mode of a digital camera, the present invention is also applicable to a system that uses another type of digital camera (e.g., a digital single lens reflex camera or a digital video camera). For example, if the present invention is applied to a digital still camera, it is possible to observe body surface tissue or observe brain tissue during craniotomy (e.g., perform a rapid brain blood flow test).

The invention claimed is:

1. An analyzing apparatus comprising:
a light source apparatus;
an image sensor that generates color image data by capturing an image of biological tissue illuminated by light generated by the light source apparatus, the color image data being RGB color image data;
an indicator calculator that calculates an indicator X that indicates a feature amount Q of the biological tissue, based on the color image data; and
a feature amount acquirer that acquires the feature amount Q based on the indicator X,
wherein the light source apparatus switches between generating light for calculating the indicator X and normal light,
the feature amount acquirer includes a contribution calculator that calculates a contribution C based on at least two colors of single-color image data included in the color image data, the contribution C quantifying a degree of contribution of scattering on a spectral characteristic of the biological tissue,
the feature amount acquirer acquires the feature amount Q based on the indicator X and the contribution C,
the contribution calculator calculates the contribution C based on color image data obtained by capturing an image of the biological tissue illuminated by the normal light as a ratio of R single-color image data to G or B single-color image data in the color image data of one frame, and
the light for calculating includes:
first light that has a continuous spectrum distributed in a first wavelength region in which light is absorbed by first and second biological substances included in the biological tissue; and
second light that has a continuous spectrum distributed in a second wavelength region in the first wavelength region,
the light source apparatus switches between generating the first light, the second light, and the normal light, and
the indicator calculator calculates the indicator X based on first observation image data G1 obtained by capturing an image of the biological tissue illuminated by the first light and second observation image data G2 obtained by capturing an image of the biological tissue illuminated by the second light,
wherein each wavelength bounding the first wavelength region and the second wavelength region is located at an isosbestic point.

2. The analyzing apparatus according to claim 1,
wherein the contribution calculator includes a storage configured to store information indicating a relationship between the feature amount Q, the indicator X, and the contribution C, and
the feature amount acquirer acquires the feature amount Q based on the information, the indicator X, and the contribution C.

3. The analyzing apparatus according to claim 2,
wherein the information is a numerical value table or a function that expresses the relationship between the feature amount Q, the indicator X, and the contribution C.

4. The analyzing apparatus according to claim 3,
wherein the information expresses a plurality of sets of the indicator X, the contribution C, and the feature amount Q, and
the feature amount acquirer selects, from the plurality of sets, a set that is closest to the indicator X and the contribution C that were calculated based on the color image data, and acquires the feature amount Q of the selected set.

5. The analyzing apparatus according to claim 4,
wherein the information expresses a plurality of sets of the indicator X, the contribution C, and the feature amount Q,
the feature amount acquirer selects, from the plurality of sets, two sets that are adjacent to the indicator X and the contribution C that were obtained based on the color image data, and
the feature amount acquirer calculates the feature amount Q using the relationship:

$$Q = \frac{X - Xb}{Xa - Xb} \cdot Qa + \frac{Xa - X}{Xa - Xb} \cdot Qb$$

where
X is an indicator calculated based on the color image data,
Qa is the feature amount of one of the two selected sets,
Xa is the indicator of one of the two selected sets,
Qb is the feature amount of another one of the two selected sets, and
Xb is the indicator of another one of the two selected sets.

6. The analyzing apparatus according to claim 1,
each of the first observation image data G1 and the second observation image data G2 is G single-color image data.

7. The analyzing apparatus according to claim 1,
wherein the feature amount Q is a molar concentration ratio of the first and second biological substances included in the biological tissue.

8. The analyzing apparatus according to claim 7,
wherein the first biological substance is oxygenated hemoglobin,
the second biological substance is reduced hemoglobin, and
the molar concentration ratio is a degree of oxygen saturation.

9. The analyzing apparatus according to claim 7,
further comprising a concentration ratio distribution image generator that, based on the feature amount Q, generates a concentration ratio distribution image that shows a distribution of the molar concentration ratio of the first and second biological substances in the biological tissue.

10. The analyzing apparatus according to claim 1,
wherein the feature amount Q is a concentration of a biological substance included in the biological tissue.

11. The analyzing apparatus according to claim 10,
further comprising a concentration distribution image generator that, based on the feature amount Q, generates a concentration distribution image that shows a distribution of the concentration of the biological substance included in the biological tissue.

12. The analyzing apparatus according to claim 11,
wherein the feature amount Q is a total hemoglobin amount of the biological tissue.

13. The analyzing apparatus according to claim 1,
further comprising an endoscope, the image sensor is provided in a distal end portion of the endoscope.

14. The analyzing apparatus according to claim 1,
wherein the first biological substance is oxygenated hemoglobin,
the second biological substance is reduced hemoglobin, and
the feature amount Q is a degree of oxygen saturation.

15. The analyzing apparatus according to claim 14,
further comprising a concentration ratio distribution image generator that, based on the feature amount Q, generates a concentration ratio distribution image that shows a distribution of the concentration ratio of the first and second biological substances in the biological tissue.

16. The analyzing apparatus according to claim 1,
wherein the feature amount Q is a total hemoglobin amount of the biological tissue.

* * * * *